United States Patent
Rand et al.

(10) Patent No.: US 10,038,300 B2
(45) Date of Patent: Jul. 31, 2018

(54) OPTICALLY-INDUCED CHARGE SEPARATION AND INDUCED MAGNETISM IN DIELECTRICS FOR OPTICAL ENERGY CONVERSION AND INTENSE MAGNETIC FIELD GENERATION

(71) Applicant: THE REGENTS OF THE UNIVERSITY OF MICHIGAN, Ann Arbor, MI (US)

(72) Inventors: Stephen C. Rand, Ann Arbor, MI (US); William M. Fisher, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 132 days.

(21) Appl. No.: 15/019,611

(22) Filed: Feb. 9, 2016

(65) Prior Publication Data

US 2016/0172822 A1 Jun. 16, 2016

Related U.S. Application Data

(62) Division of application No. 13/810,621, filed as application No. PCT/US2011/036597 on May 16, 2011, now Pat. No. 9,274,045.

(Continued)

(51) Int. Cl.
*H01S 3/00* (2006.01)
*H01S 5/04* (2006.01)
(Continued)

(52) U.S. Cl.
CPC ............. *H01S 5/041* (2013.01); *G01N 21/21* (2013.01); *G02F 1/09* (2013.01); *G02F 1/3534* (2013.01);
(Continued)

(58) Field of Classification Search
CPC ........................... G02F 2203/13; G01R 33/26
See application file for complete search history.

(56) References Cited

U.S. PATENT DOCUMENTS 5,522,944 A   6/1996 Elazari
6,472,869 B1 * 10/2002 Upschulte .............. G01R 33/26
                                                         324/300
(Continued)

OTHER PUBLICATIONS

Graf et al., "High-Frequency Electrical Pulse Generation using Optical Rectification in Bulk GaAs," Applied Physics Letters 76(19):2647-2649 (2000).

(Continued)

*Primary Examiner* — Thanh Luu
(74) *Attorney, Agent, or Firm* — Marshall, Gerstein & Borun LLP

(57) ABSTRACT

Schemes are described to produce quasi-static charge separation, Terahertz radiation, and programmable magnetic field generation using linearly-polarized light in unbiased, transparent insulators. The methods exploit a recently-observed magneto-electric optical nonlinearity that produces intense magnetization in undoped, homogeneous dielectrics. Analysis reveals that strong magnetic effects can be induced at modest optical intensities even with incoherent light. Consequently, efficient solar power conversion is feasible without the semiconductor processing or electron-hole pair generation that is required in conventional photovoltaic cells. Additionally, conditions and techniques are described to generate intense THz radiation in unbiased substrates and large magnetic fields orientated transverse to the direction of propagation of light, without the need for any external permanent magnetic or electromagnetic apparatus.

10 Claims, 13 Drawing Sheets

Related U.S. Application Data

(60) Provisional application No. 61/334,994, filed on May 14, 2010.

(51) Int. Cl.

| | |
|---|---|
| *H02M 7/06* | (2006.01) |
| *G01N 21/21* | (2006.01) |
| *H01S 5/022* | (2006.01) |
| *G02F 1/09* | (2006.01) |
| *G02F 1/35* | (2006.01) |
| *H02M 7/00* | (2006.01) |
| *H02J 7/02* | (2016.01) |
| *H02J 7/32* | (2006.01) |

(52) U.S. Cl.
CPC ......... *H01S 5/02236* (2013.01); *H02M 7/003* (2013.01); *H02M 7/06* (2013.01); *G02F 2203/13* (2013.01); *H02J 7/022* (2013.01); *H02J 7/32* (2013.01); *Y02E 10/56* (2013.01)

(56) References Cited

U.S. PATENT DOCUMENTS

| | | |
|---|---|---|
| 6,747,736 B2 | 6/2004 | Takahashi |
| 7,283,704 B2 | 10/2007 | Furuya et al. |
| 2008/0314438 A1 | 12/2008 | Tran et al. |

OTHER PUBLICATIONS

International Search Report and Written Opinion from PCT/US2011/036597 dated Aug. 31, 2011.

Oliveira, et al. "Intense Nonlinear Magnetic Dipole Radiation at Optical Frequencies: Molecular Scattering in a Dielectric Liquid," Physical Review Letters 98:093901-1 to 093901-4 (2007).

Rand, "Quantum Theory of Coherent Transverse Optical Magnetism," J. Opt. Soc. Am 26(12):B120-B129 (2009).

Rand, et al. "Optically Induced Magnetization in Homogeneous, Undoped Dielectric Media," J. Opt. Soc. Am 25(7):1106-1117 (2008).

Wang, "Generation of Terahertz Radiation via Nonlinear Optical Methods," IEEE Transactions on Geoscience and remote Sensing 1(1):1-5 (2002).

\* cited by examiner

OPTICALLY-INDUCED CHARGE SEPARATION AND INDUCED MAGNETISM IN DIELECTRICS FOR OPTICAL ENERGY CONVERSION AND INTENSE MAGNETIC FIELD GENERATION

CROSS-REFERENCE TO RELATED APPLICATIONS

This application is a Divisional of U.S. application Ser. No. 13/810,621, filed Jul. 25, 2013, entitled "Optically-Induced Charge Separation and Induced Magnetism in Dielectrics for Optical Energy Conversion and Intense Magnetic Field Generation," which is a U.S. National Phase of PCT/US2011/36597, filed May 16, 2011, entitled "Optically-Induced Charge Separation and Induced Magnetism in Dielectrics for Optical Energy Conversion and Intense Magnetic Field Generation," which claims the benefit of U.S. Provisional Application Ser. No. 61/334,994, filed May 14, 2010, entitled "Optically-Induced Charge Separation And Induced Magnetism In Dielectrics For Optical Energy Conversion And Intense Magnetic Field Generation," the entirety of which is hereby incorporated herein by reference, including the appendices filed in that application.

BACKGROUND

Recent experiments have shown that intense magnetic dipole radiation can be generated with light at intensities as low as $10^7$ W/cm$^2$ in transparent dielectrics. This surprising phenomenon has been shown to take place via a magneto-electric interaction that was overlooked in the early days of nonlinear optics and overcomes the apparent limitations on magnetic dipole (MD) effects imposed by the multipole expansion of classical electrodynamics. The phenomenon is essentially relativistic in origin but appears at sub-relativistic intensities because of parametric enhancement. Classical analysis, numerical simulations, perturbation theory, and quantum theory have been offered to analyze and explain this phenomenon. These treatments describe an oscillatory, transverse magnetic response that is driven by the product of the electric and magnetic field components of a linearly-polarized light field. The fields act jointly (despite their orthogonality) to drive a coherent dipolar magnetization in bound electron systems. Strong coupling of energy from electric to magnetic motions accounts for the appearance of large magnetic dipole (MD) moments despite the weakness of optical Lorentz forces at intensities far below the relativistic threshold ($I<<10^{18}$ W/cm$^2$).

SUMMARY OF THE INVENTION

In an embodiment, an optically-pumped AC current or voltage source comprises: a non-conducting transparent substrate; a laser source coupled to supply a laser output into the substrate, the laser output having an intensity above a threshold for inducing saturated dipole magnetization in the substrate; a switch for switching the direction of propagation of the laser output supplied to the substrate between a forward direction and a backward direction propagating through the substrate, at a rate $\Omega$; and a circuit coupled across the substrate to receive and convert an electrical AC charge oscillation, generated by the laser output supplied to the substrate, into a DC current for supplying a load.

In another embodiment, an AC current or voltage source comprises: a non-conducting substrate; and a light source collector positioned to receive light from a non-coherent light source and to pump a light output into the substrate, the light output having an intensity level approaching or above a threshold for inducing a maximum magnetic response in the substrate to produce charge separation across the substrate.

In yet another embodiment, an opto-electrical converter comprises: a non-conducting transparent substrate having electrodes across at least a portion thereof; and a light source coupled to pump a light beam into the substrate, the beam having an energy level above a threshold for inducing maximum magnetic response in the substrate to produce charge separation across the substrate.

In another embodiment, an AC current or voltage source comprises: a semiconducting substrate; a pump light source producing a pump light output having a wavelength or wavelengths selected to lie within a forbidden energy gap such that absorption by host valence-conduction band or homo-lumo transitions is avoided the pump light output having an intensity above a threshold for inducing maximum magnetic response in the substrate to produce charge separation across the substrate; a switch for switching the direction of propagation of light within the substrate between forward and backward directions through the substrate, at rate of $\Omega$; and a circuit coupled to electrodes across the substrate to receive and convert the electrical AC charge oscillation into a current for supplying a load.

In another embodiment, an optically-pumped terahertz radiation source comprises: an unbiased, non-conducting transparent substrate; a laser source coupled to pump a pulsed laser output into the substrate, the laser pulses having a peak intensity for each pulse above a threshold for inducing saturated dipole magnetization and charge separation in the substrate; and said laser pulses having a pulse duration of less than one picosecond so that the spectrum of impulsive charge separation in the substrate extends to at least a frequency of one terahertz, 1 THz.

In yet another embodiment, a reconfigurable magnetic field generator comprises: an unbiased, non-conducting transparent substrate; a laser source coupled to pump laser output into the substrate, the laser output having an intensity above a threshold for inducing saturated dipole magnetization in the substrate; an optical modulator to control the pump laser output distribution in space, time, and frequency to effect a desired variation of an induced B field amplitude in the substrate; and a programmable controller to control the modulator to control the distribution of the laser output and to produce a desired modulation of laser output cross-sectional and temporal intensity.

In yet another embodiment, a DC charge generator comprises: a substrate; a pump light source producing a pump light output having an intensity above a threshold for inducing maximum magnetic response in the substrate to produce charge separation across the substrate; and electrodes positioned adjacent the substrate to receive a DC voltage resulting from the conversion of the pump light output into the charge separation.

BRIEF DESCRIPTION OF THE DRAWINGS

FIG. 1A plots motion for incident electric field strength of $E_0=1$ V/m, where there is an enormous difference of scales on the x and z axes. FIG. 1B plots motion for incident electric field strength of $E_0=10^8$ V/m, where the scales on the x and z axes are almost the same. Frequency and linewidth parameters were chosen to be $\omega_0 = \Gamma_{12}^{(e)} = \Gamma_{12}^{(m)} = 1$ and $|\Delta_1/\Gamma_{12}^{(e)}| = 0.3$.

FIG. 2A plots the x axis component of motion versus time. FIG. 2B plots the z axis component as a function of time, calculated for $E_0 = 10^8$ V/m and $\tau_{coh} = \infty$. All frequency and linewidth parameters were set to unity.

FIG. 3A plots the x axis versus time. FIG. 3B plots the z axis as a function of time, calculated for $E_0 = 10^8$ V/m and an average phase disruption time of $\tau_{coh} = 30$ fs. All frequency and linewidth parameters were set to unity.

FIG. 4A plots the x axis versus time. FIG. 4B plots the z axis versus time, calculated for $E_0 = 10^8$ V/m and an average phase disruption time of $\tau_{coh} = 3$ fs. All frequency and linewidth parameters were set to unity.

FIG. 5A plots x axis versus time; FIG. 5B plots y axis versus time; and FIG. 5C plots the z axes versus time, calculated for $E_0 = 10^8$ V/m and an average phase and polarization disruption time of $\tau_{coh} = 3$ fs. All frequency and linewidth parameters were set to unity.

DETAILED DESCRIPTION

Figure 1A:
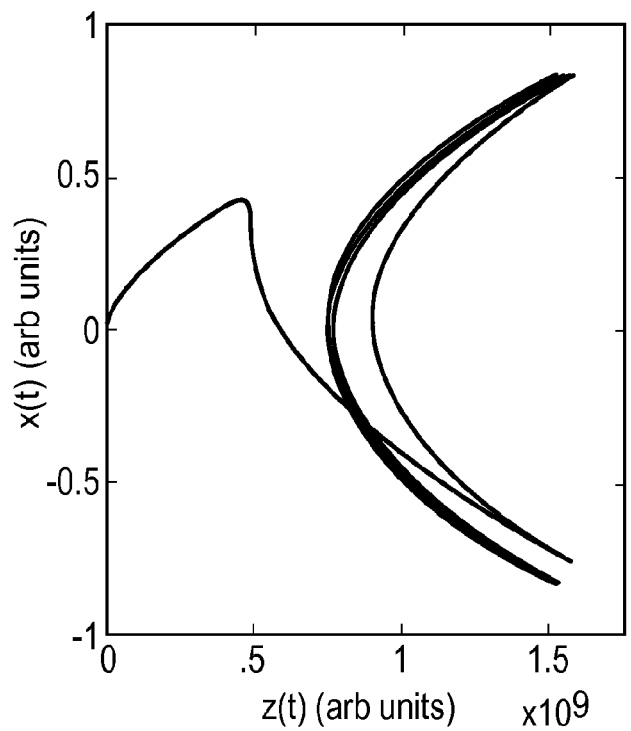
FIGS. 1A and 1B illustrate plots showing the trajectory of optically-driven electron motion determined by numerical integration, showing motion along an x and z axis.

The present invention describes various embodiments that, under suitable conditions as described, exploit two phenomena that accompany optically-induced magnetism to form altogether new types of devices. One class of device exploits the formation of a relatively large, quasi-static charge displacement induced into dielectric media, via pumping with light of specified conditions. Conditions have been identified for inducing a strong electric dipole moment along the propagation direction of incident linearly-polarized light functioning as a pump beam. The devices, for example, are then able to achieve a unique form of optical power conversion within dielectric media. A second class of device produces a large transverse magnetic field in transparent dielectric or semiconducting media. Conditions are identified for creating fields greater than 1 Tesla with light. The resulting devices may be used for the control of spin orientation as well as for reading, writing and erasing magnetic memories.

More particularly, techniques are described for optical energy conversion from coherent or stochastic incident light fields, and which may be used to provide entirely new classes of devices and new applications of use. For example, charge separation applications include the formation of photon pumped charged bodies, photon pumped DC and AC voltage generation, DC and AC current generation, solar cells and panels, and terahertz (THz) radiation sources. Other applications may be characterized as purely magnetic since they enable magnetic dipole radiation sources and intense oscillatory magnetic field sources.

The charge separation techniques may convert an insulating photonic material that supports displacement currents, rather than ordinary conduction, into an electrical power source. For example, magneto-electric optical processes can produce small displacement currents within these insulating materials. At high frequencies of the input beam, these displacement currents can be used to form photovoltaic power sources that rival the efficiency of semiconductor-based devices common in solar applications (e.g., solar panels, solar cells, etc.). The present techniques can also provide a new way of generating Tesla-level magnetic fields within materials that are normally non-magnetic, and of producing static charge separation in materials not currently recognized as photovoltaics.

The optical magnetic techniques described herein may be used for magnetic storage, magnetic sensor technology, spintronics, quantum information science, and have important implications for inertial confinement fusion and renewable energy technology. Experiments to date have shown for example that magnetic dynamics become important at optical intensities of only $10^8$ W/cm$^2$, far below the generally accepted threshold which is that of relativistic optics around $10^{18}$ W/cm$^2$. Hence, the ability to create optical magnetism at low intensities enables new magnetic technologies without requiring relativistic conditions or current-carrying apparatus.

Techniques described herein are able to identify threshold conditions for establishing the photon-induced charge separation and magnetic light sources in various materials, including identifying suitable materials and optimizing conditions for those materials.

Without limitation as to the discussed subject matter, it is believed that the underpinning conditions created by the present techniques operate as follows. Numerical simulations of charge motion responding to the driving forces of incident light show that upon proper photon pumping conditions magneto-electric interactions result in the centroid of electron motion shifting away from the nucleus. Each atom or molecule affected by the pumped beam thereby acquires a large static dipole moment, while undergoing driven harmonic motion. This static polarization can be continuously sustained by steady illumination and can be described as a sequence of events. First, the electric field initiates motion of electrons from rest, in a direction parallel to the electric field. Then the magnetic component of the light field causes a deflection of the electron around its axis. This small deflection due to the Lorentz force grows rapidly in amplitude as the result of parametric enhancement and the average position of the electron shifts away from the nucleus as well. A large oscillating magnetic moment appears and generates intense magnetic dipole radiation and a large oscillating magnetic field. The formation of a large static electric dipole along the axis of propagation is furthermore symptomatic of magnetic energy storage in the medium.

The result of these steps is that an optically-charged capacitor is formed that has the potential to provide an efficient source of electrical energy. To achieve efficient photon induced charge separation, a pump beam formed of a train of femtosecond pulses may be used. For pulses of sufficiently short duration, the quasi-static electric dipole that results from each pump pulse interaction has a transient character that produces radiation at THz frequencies. Pulses of duration $\tau_p < 100$ fs are capable of generating radiation with a bandwidth of $\Delta v \approx (1/\tau_p)$, which is well into the THz range. Consequently both optical charge separation and magnetically-induced THz radiation result under proper pumping conditions. On this basis, a photovoltaic generator was designed, one that differs from conventional solar cells in that the generator does not require absorption of the incident light or the generation of free electrons. Voltage generation occurs from the forces exerted on bound charges by the pump beam, without these conditions.

Charge Separation

To demonstrate induced charge separation in bound electron systems, we considered a closed system of identical 2-level atoms or molecules with a resonance frequency $\omega_0 = (\omega_2 - \omega_1)$. The atoms are subjected to an electromagnetic plane wave of frequency $\omega$ that propagates in the positive z-direction. The light is assumed to be linearly-polarized along $\hat{x}$ and detuned from resonance by $\Delta_1 \equiv \omega_0 - \omega$. Population dynamics and coherences are found using the master equation for the density matrix $$i\hbar\dot{\rho} = [H,\rho] - i\hbar\dot{\rho}_{relax}. \qquad (1)$$

The system Hamiltonian $H = H_o + V(t)$ is assumed to consist of a static part $$H_0 = \hbar\omega_1|1\rangle\langle 1| + \hbar\omega_2|2\rangle\langle 2| + \hbar\omega_3|3\rangle\langle 3|, \qquad (2)$$

which describes the unperturbed diagonal matrix elements of the static Hamiltonian and an optical interaction $V(t)$ of the combined dipole form $$V = -\bar{\mu}^{(e)} \cdot \bar{E} - \bar{\mu}^{(m)} \cdot \bar{B}. \qquad (3)$$

$\dot{\rho}_{relax}$ represents phenomenological relaxation of individual density matrix elements in the Schrodinger picture. Uppercase rate constant $\Gamma_{12}$ describes coherence decay between levels 1 and 2 and the lowercase constant $\gamma_{22}$ is population decay rate of the excited state. The system is taken to be a nominally 2-level system (with levels 1 and 2), but each level is assumed to have some number of sub-levels of which 3 is an example in Eq. 2 above. The irreducible forms of the (polar) electric and (axial) magnetic components of the optical wave are $$\bar{E}(t) = -\tfrac{1}{2}[E_+\hat{\epsilon}_- + E_-\hat{\epsilon}_+]e^{i\phi} + h.c., \qquad (4)$$

$$\bar{B}(t) = -i/2[B_+\hat{\epsilon}_- - B_-\hat{\epsilon}_+]e^{i\phi} + h.c. \qquad (5)$$

In these expressions $\phi \equiv \omega t - kz$ is the optical phase and the circular basis vectors $\hat{\epsilon}_\pm = -(\hat{x} \pm i\hat{y})/\sqrt{2}$ are components of the rank one spherical tensor. h.c. denotes the Hermitian conjugate. Carets designate unit basis vectors. For linear polarization along $\hat{x}$, the field amplitudes $E_0$, $B_0$ are related to those in Equations (4) and (5)

$$E_+ = E_- = E_0/\sqrt{2}, \qquad (6)$$

and $B_+ = B_- = B_0/\sqrt{2}$, since the circular components must then have equal amplitudes. The irreducible electric and magnetic dipole moments induced by the field have magnitudes and directions given by $$\bar{\mu}^{(e)} = -(\mu_-^{(e)}\hat{\epsilon}_+ + \mu_+^{(e)}\hat{\epsilon}_-), \qquad (7)$$

and $$\bar{\mu}^{(m)} = -i(\mu_+^{(m)}\hat{\epsilon}_- - \mu_-^{(m)}\hat{\epsilon}_+), \qquad (8)$$

respectively. When the circular components $\mu_\pm$ of these moments are equal, the electric and magnetic moments themselves point along $\hat{x}$ and $\hat{y}$, parallel to the inducing fields.

Substitution of Equations (4-8) into Equation (3) furnishes the interaction Hamiltonian and a solution for the electric and magnetic dipole moments induced in the medium. The use of Equations (2) and (3) in Equation (1) then permits solution of the density matrix $\rho(t)$. The polarization driven by the combined action of the electric and magnetic fields in the medium is examined by calculating the expectation values of the corresponding electric and magnetic dipole moments. To calculate them, standard perturbation theory can be applied, introducing the electric field perturbation in first order and the magnetic interaction in second order. One obtains the results $$\rho_{13}(2\omega) = \frac{1}{2} \frac{[\Omega_0^{(e)}]_{12}[\Omega_0^{(m)}]_{23}}{(\Delta_1 + i\Gamma_{12}^{(e)})(\Delta_2 + i\Gamma_{13}^{(m)})} e^{2i\omega t} \qquad (9a)$$

$$\rho_{13}(\omega = 0) = \frac{1}{2} \frac{[\Omega_0^{(e)}]_{12}[\Omega_0^{(m)}]_{23}^*}{(\Delta_1 + i\Gamma_{12}^{(e)})(\omega_\varphi + i\Gamma_{13}^{(m)})} \qquad (9b)$$

where $\Delta_1 = \omega_0 - \omega$ is the detuning of the optical wave from the electric dipole resonance at frequency $\omega_0$ and $\Delta_2 = \omega_\varphi - 2\omega$.

For linear input polarization beam, the steady-state electric dipole of a system of N molecules per unit volume is found to be $$\bar{P}(\omega = 0) = N\hat{z}(\mu_{31}^{(e)}\rho_{13}(\omega = 0) + h.c.) \qquad (10)$$

$$= N\hat{z}\left(\frac{1}{2}\frac{\mu_{31}^{(e)}[\Omega_0^{(e)}]_{12}[\Omega_0^{(m)}]_{23}^*}{(\Delta_1 + i\Gamma_{12}^{(e)})(\omega_\varphi + i\Gamma_{13}^{(m)})} + h.c.\right)(\rho_{11} - \rho_{22}).$$

Similarly, the radiant magnetic dipole moment or optical magnetization is give by:

$$\tilde{M} = -\hat{y}N\left(\frac{e}{m}\right)\left[\frac{\langle 3|L_y|1\rangle[\Omega_0^{(e)}]_{12}[\Omega_0^{(m)}]_{23}}{(\Delta_1 + i\Gamma_{12}^{(e)})(\Delta_2 + i\Gamma_{13}^{(m)})} + \frac{\langle 3|L_y|1\rangle^*[\Omega_0^{(e)}]_{12}^*[\Omega_0'^{(m)}]_{23}^*}{(\omega_\varphi + i\Gamma_{12}^{(e)})(\Delta_2 + i\Gamma_{13}^{(m)})}\right] \quad (11)$$

$$(\rho_{11} - \rho_{22})$$

Factors in the numerators of Equations (10) and (11) are Rabi frequencies defined by $\Omega_0^{(m)}=\mu^{(m)}B_0/2\hbar$, $\Omega_0^{(e)}=\mu^{(e)}E_0/2\hbar$, and $\Omega'_0^{(m)}=\mu^{(m)}B^*_0/2\hbar$. Equation (10) consists of a zero frequency term that predicts a static charge separation induced by light in dielectric media illuminated by moderately intense light. Since it contains a parametric detuning factor $(\Delta_2+i\Gamma_{12}^{(m)})^{-1}$, where $\Delta_2=\omega_\varphi-2\omega$, and a second detuning of $\omega_\varphi=\omega_3-\omega_1$ which is a ground state rotational frequency and should be very small, its magnitude can be dynamically-enhanced. These factors in the denominator account for a large magnitude for charge separation and THz emission effects of interest when the electric transition between states 1 and 2 and the magnetic transition between states 2 and 3 are allowed. In Eq. (11) the angular momentum matrix element must also be non-zero. These requirements can be met when states 1 and 2 differ by $l_2-l_1=\pm 1$ and significant admixture of the ground state into the excited state takes place by the action of the electric field, so that finally the sub-states on the 2 to 3 transition need to differ only in magnetic quantum numbers by $m_3-m_2=\pm 1$. If the molecular point symmetry of the medium includes inversion, then parity is a good quantum number. To satisfy the need for states 1 and 2 to have opposite parity for the electric dipole transition and for states 2 and 3 (where 3 is a ground state sub-level) to have the same parity so that $\langle 1|x|2\rangle \neq 0$ and $\langle 3|L_y|1\rangle \neq 0$ the intense optical E field must mix the parity of states 1 and 2. Then the dynamic magnetization can form regardless of the point symmetry of the molecules comprising the medium. Equation (11) gives the amplitude of the induced optical magnetization via the expression $M(t)=\frac{1}{2}\tilde{M}e^{i\Phi}+h.c.$ and the accompanying magnetic field through the constitutive relation $B=\mu_o H+M$. On the other hand, a static dipole can only form in the medium if there is no inversion symmetry. The reason for this is that when inversion symmetry is present, electric dipoles can only form between initial and final states of opposite parity. But if states 1 and 2 support an allowed electric dipole transition in the first step of the two-step process that produces coherence between states 1 and 3, then states 1 and 3 are forced to have the same parity. To prevent this, and permit formation of a static electric dipole between the two ground states 1 and 3, the molecules of the converter medium must not have inversion symmetry.

Charge Separation in Coherent Fields

To visualize how optically-induced charge separation can take place in atoms, Newton's equation F=ma for the motion of a bound electron may simply be integrated with respect to time to follow the actual trajectory of an electron driven by the light field in real space. For this purpose, classical theory is perfectly adequate provided that the incident light beam does not induce population changes or generate free charge carriers. Consequently in the simulations that follow, the driving field is detuned and the resonance itself is de-emphasized by choosing a radiative damping constant that is equal to the optical frequency itself ($\Gamma_{12}^{(e)}=\omega$). In this way strong coupling to the path is assured and the incident field is elastically scattered rather than absorbed.

Figure 1B:
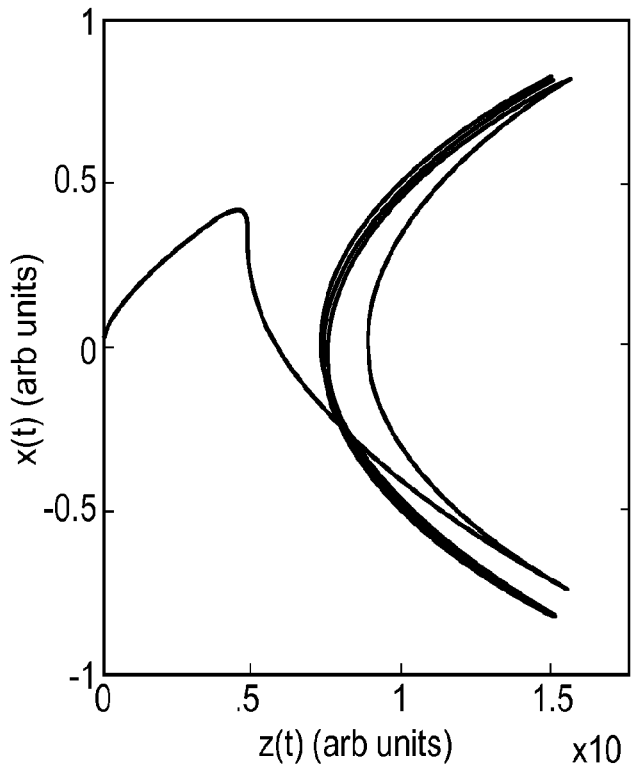

FIGS. 1A and 1B present two electron trajectories calculated by direct integration of the classical harmonic oscillator model including the magnetic Lorentz force. In each plot, the frequency is detuned from electronic resonance by $\Delta_1/\Gamma_{12}^{(e)}=0.3$. FIG. 1A is calculated for an incident plane wave field of field strength $E_0=1$ V/m; and FIG. 1B is for an incident field strength $E_0=10^8$ V/m. In the first case, at low field strength, the trajectory lies almost entirely along the x-axis of the electric field, as expected. Motion driven by the electric field dominates. Magnification of the horizontal scale by $10^9$ is necessary to make the component of the motion in the direction of propagation of light (i.e., along the z-axis) large enough to see, and this z axis component originates simply from the Lorentz force. In contrast, in FIG. 1B, the horizontal scale showing the z-axis component of the electron motion driven by a pump beam is nearly equal to that of the x-axis; the z-axis component has only been magnified by an order of 10 as compared to the x-axis component. Thus, for the higher intensity pump beam, the motion along z-axis develops an amplitude comparable to that of motion along x-axis.

It can be seen from FIGS. 1A and 1B that motion reaches a steady state after only a few periods, meaning that transient response is very short-lived. The electron follows a strongly curved path and the centroid of the electron motion is displaced forward along the direction of propagation, away from the nucleus located at x=y=z=0. Although both E and B oscillate harmonically at the optical frequency and therefore have an average value of zero, E is a polar vector that reverses sign upon inversion, whereas B is an axial vector which does not. In combination, it is evident that these field components can drive a static displacement of bound electrons with respect to the nucleus. The exchange of energy that takes place between the electric and magnetic degrees of freedom in the system is not reversible as it is in most coupled oscillator systems. The overall optical interaction at intermediate (sub-relativistic) intensities yields an electric dipole (ED) moment on an ultrafast timescale which is quasi-static and intensity-dependent. The large amplitude of this effect reflects parametric oscillation driven by the doubled frequency of electron motion along the z axis (FIGS. 2B, 3B, 4B, and 5C), consistent with the fact that the dynamics may be described by a complex Mathieu equation.

Charge Separation in Stochastic Fields

The charge separation effect described in the preceding section assumed that the pump beam, or light field, was monochromatic and smoothly varying (sinusoidal) in time. However, nearly the same magnitude of charge separation is possible with phase- and polarization-disrupted fields. The temporal variations of E and B in such light fields are nearly completely chaotic or random and they are called "stochastic." Sunlight is an example of a stochastic light field.

Figure 2A:
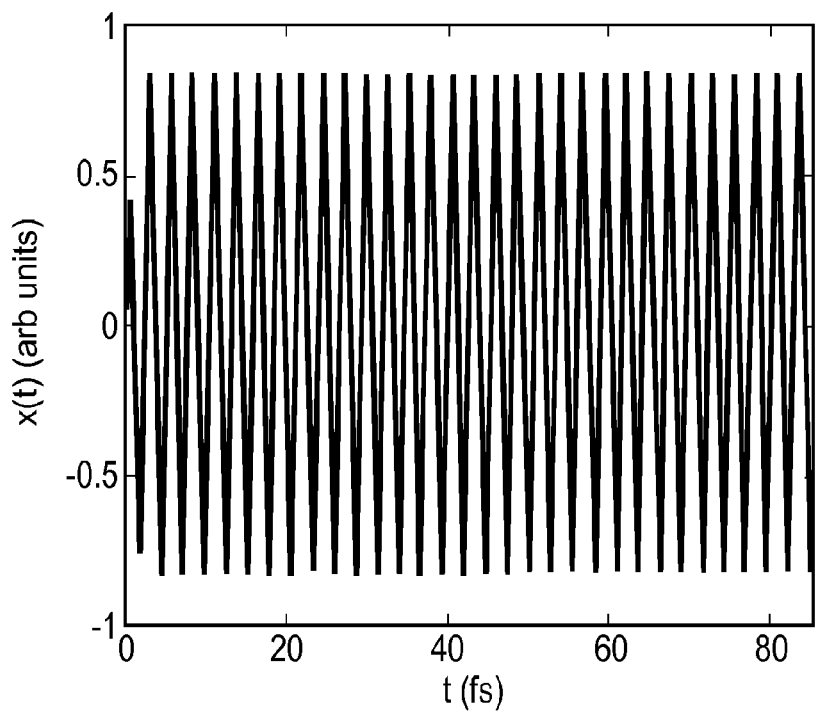
FIGS. 2A and 2B illustrate plots of cartesian components of electron motion along different axes as a function of time.
Figure 2B:
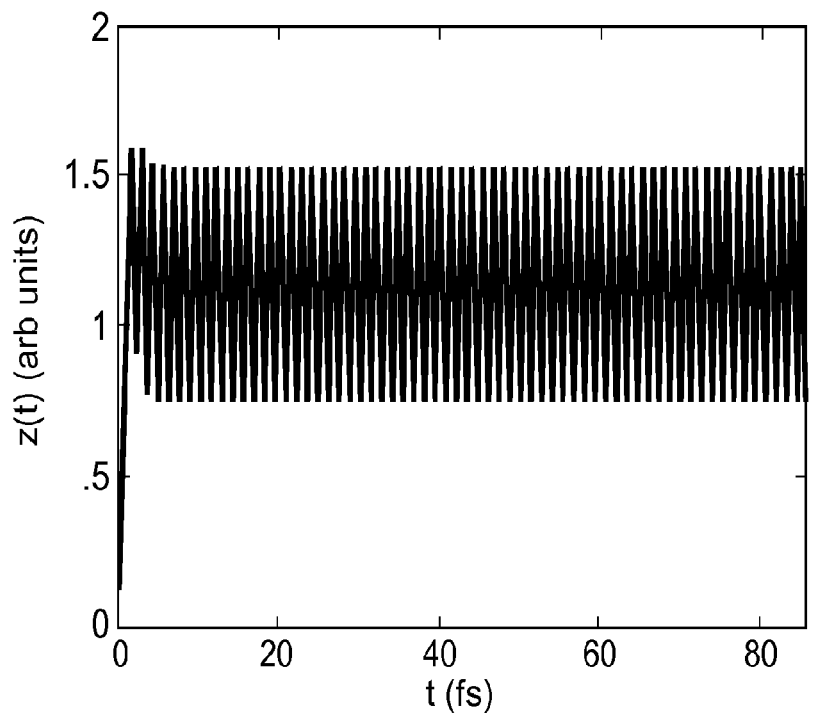

The charge trajectories in FIGS. 1A and 1B were obtained by assuming that the driving field was completely coherent ($\tau_{coh}=\infty$). For a stochastic light field as the incident radiation, the system undergoes a forced oscillation that continues without variation after a brief transient. Cartesian components of the motion therefore vary harmonically at long times as illustrated in FIGS. 2A and 2B. The motion along the x-axis and z-axis are plotted separately in FIGS. 2A and 2B for clarity, and reveal that the projection of circular motion on the z-axis doubles its frequency. These calculations provide a point of comparison with the driven response to stochastic fields that are considered herein.

Figure 3A:
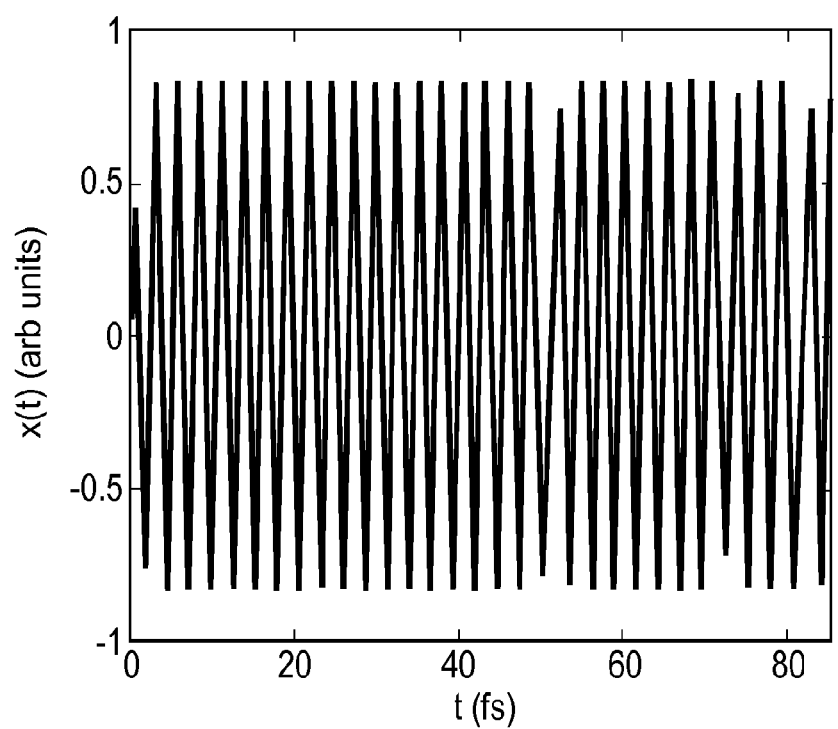
FIGS. 3A and 3B illustrate plots of cartesian components of electron motion along different axes as a function of time.
Figure 3B:
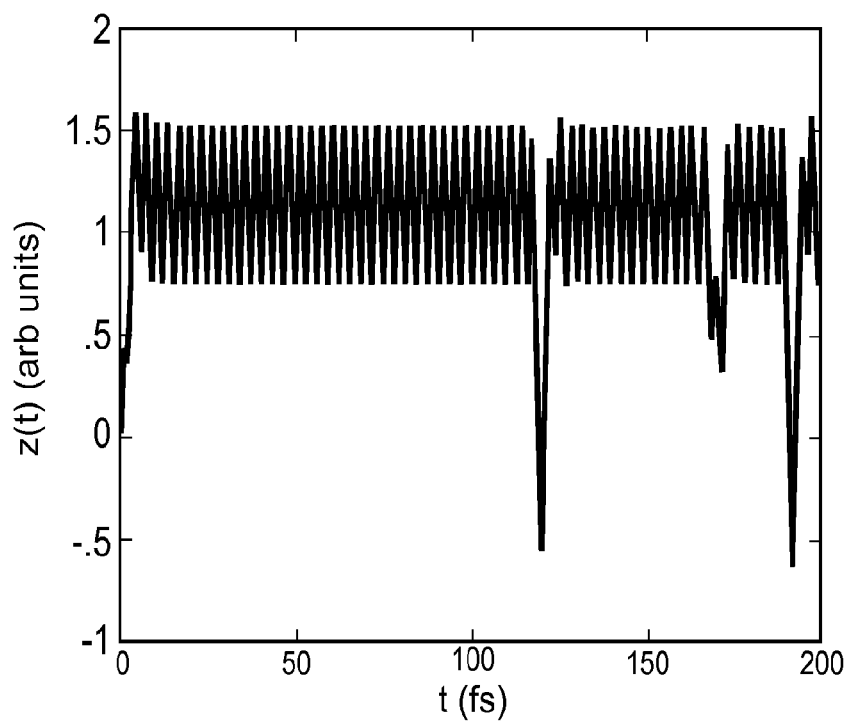
Figure 4A:
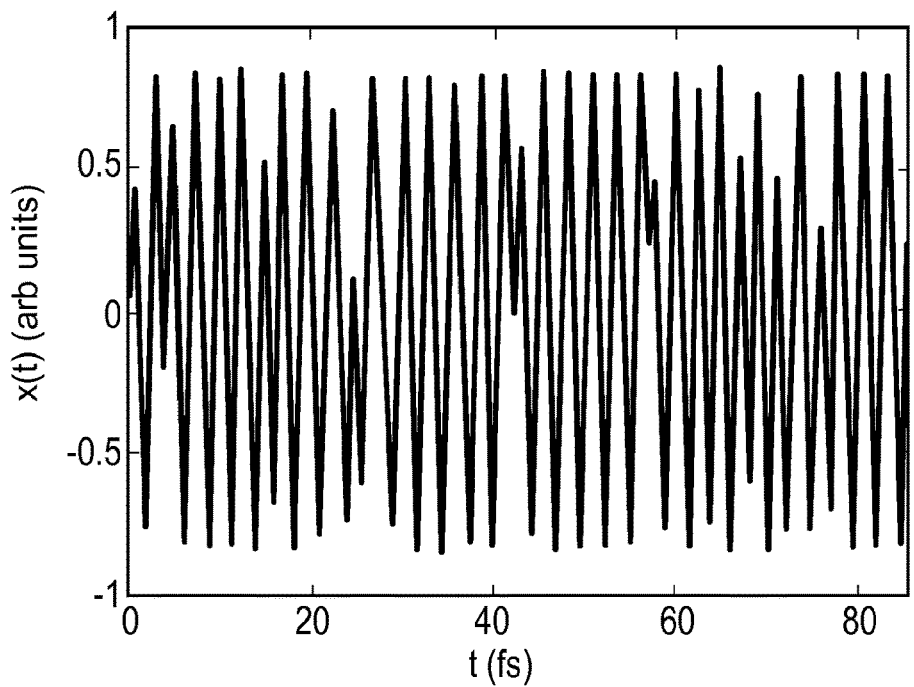
FIGS. 4A and 4B illustrate plots of cartesian components of electron motion along different axes as a function of time.
Figure 4B:
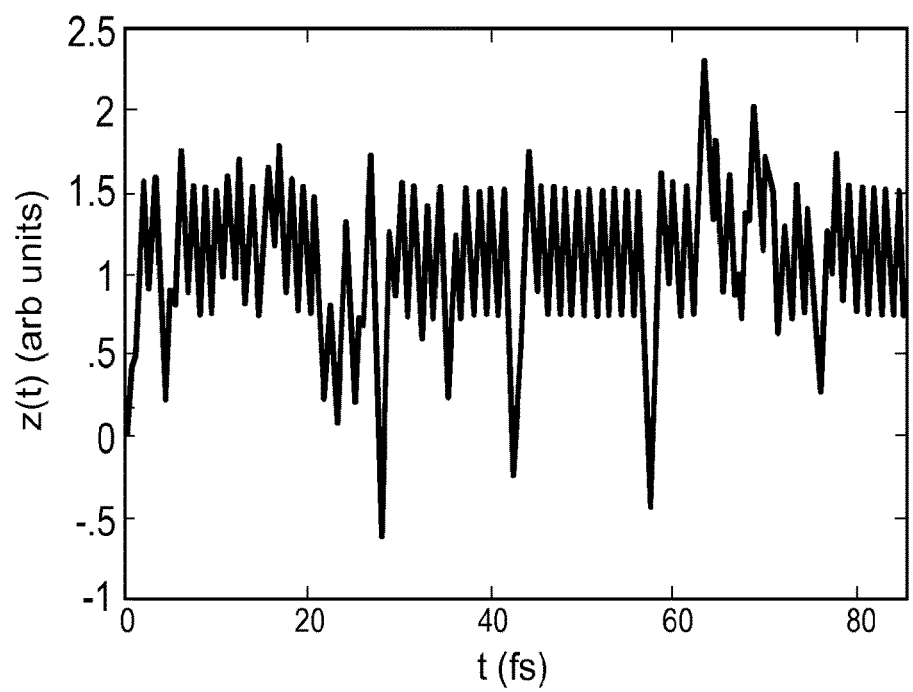

To follow charge motion driven by a random light field, an Euler integration technique that employed a constant temporal step size was used. The stochastic character of sunlight was simulated by changing the phase of the driving fields by an amount in the range $0$-$2\pi$ at an average rate of $\tau_{coh}^{-1}$. Six hundred and twenty-eight integration steps were performed per optical cycle. This permitted precise variation and specification of the coherence time. For example, at a wavelength of 800 nm the optical period is 2.6 fs, so a coherence time of 30 fs can be modeled accurately by randomly changing phase at an average rate of once per 7222 steps. The effect of a stochastic driving field with $\tau_{coh}=30$ fs is presented in FIGS. 3A and 3B. When the dephasing time was reduced to 3 fs to correspond specifically to radiation from the sun, the results in FIGS. 4A and 4B were obtained. Note that in both FIGS. 4A and 4B a large, positive offset of the average motion is still evident in the direction of propagation, despite dephasing at rates approaching the optical frequency.

Figure 5A:
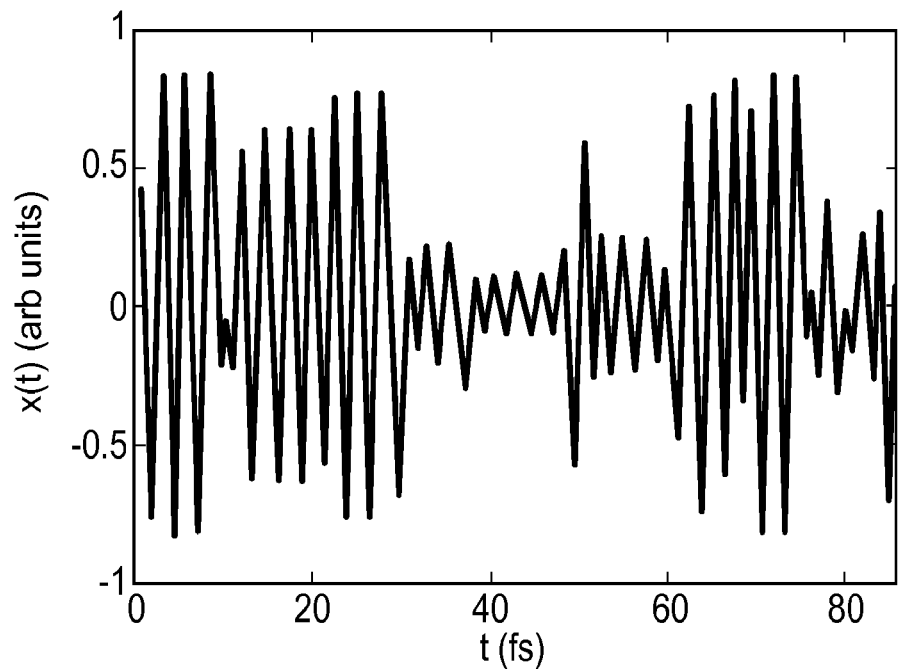
FIGS. 5A, 5B, and 5C illustrate plots of cartesian components of electron motion along different directions as a function of time.
Figure 5B:
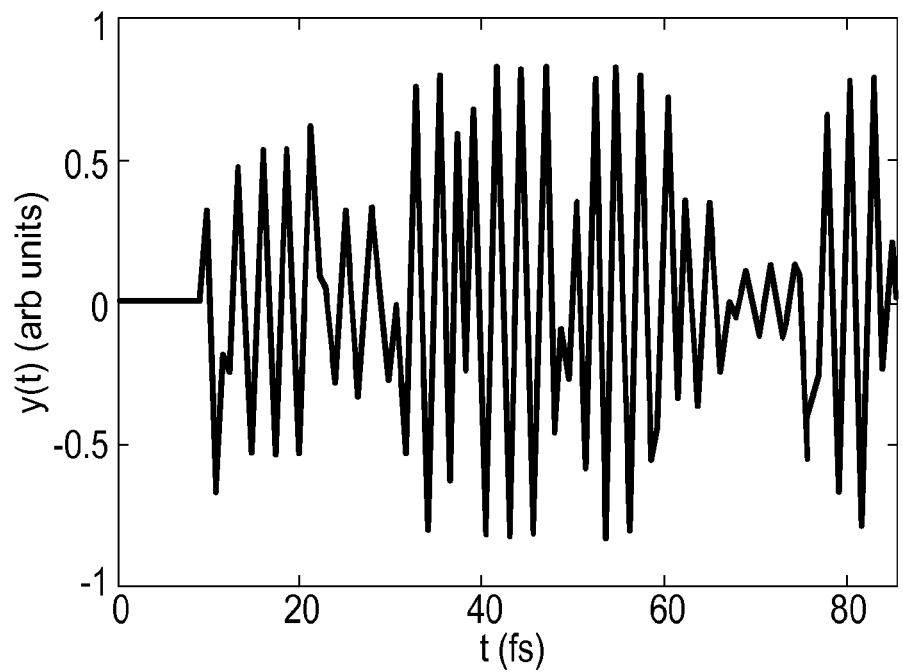
Figure 5C:
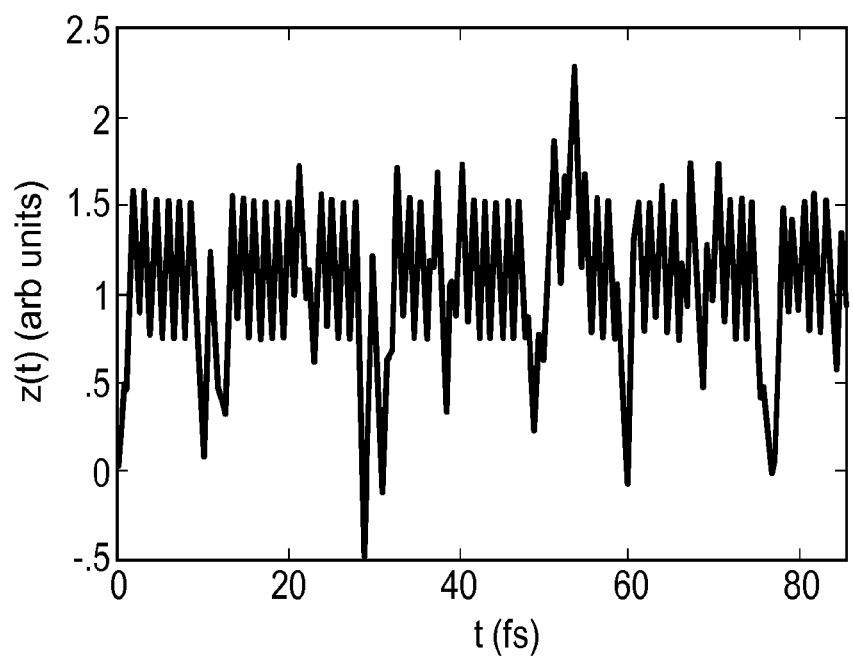

Sunlight exhibits rapid, random fluctuations both in phase and polarization. To simulate radiation from this source fully, the procedure described above must therefore be generalized to include stochastic polarization fluctuations. Allowance for random polarizations in the x-y plane necessitates the use of three dimensions. Consequently in FIGS. 5A-5C the projection of the electron trajectory along y is presented in addition to the components along the x-axis and the z-axis. Polarization jumps were assumed to take place at the same time as phase jumps, but were based on a separate random number selection. FIGS. 5A and 5B jointly furnish a map of the electron motion in the transverse plane. By comparing these two plots, one discovers that decreases in the amplitude of motion along the x-axis are invariably accompanied by increases in the amplitude along the y-axis and vice versa. In FIG. 5C, the motion along the z-axis remains similar to that when phase-only disruptions are taken into account. While larger, random excursions and oscillations are evident in FIG. 5C, the average offset remains nearly the same as before.

Optical-to-Electrical Power Conversion

The charge separation described above saturates when the magnetic current density $J_M$ attains its maximum value, namely one half the electric displacement current $J_E$. At higher levels of excitation than this, in the so-called saturation regime, the magnetic susceptibility is then $$\chi^{(m)}=-\tfrac{1}{2}\chi^{(e)}, \quad (12)$$

and the longitudinal polarization established by it is proportional to the electric field, just like the usual transverse polarization induced by the electric field component of light. With Equation (12), predictions can be made of the surface charge density attainable in a plane-parallel dielectric slab illuminated uniformly with a specified intensity of coherent light, without knowledge of the linewidth parameters, detunings and transition moments in Equation (10). With this information, the electric energy density that can be stored in a magnetic "optical battery" may be accurately estimated.

The energy U stored in a magnetic optical battery can be calculated by imagining a simple parallel plate capacitor formed by a dielectric slab of thickness L and permittivity e through which the light propagates. Then, as is well-known, $$U=\tfrac{1}{2}CV^2, \quad (13)$$

where C is the capacitance and V is the voltage that develops across the slab due to irradiation. The displacement charge Q that develops is given by the beam area A times the induced surface charge density $\sigma_s$.

$$Q=\sigma_s A \quad (14)$$

The magnitude of any surface charge density is the same as the polarization P per unit volume that causes it. Hence, making use of (12) and the standard formula for the capacitance of a dielectric slab, we have $$V=\frac{Q}{C}=\frac{\sigma_s A}{\varepsilon A/L}=\frac{P^{(m)}L}{\varepsilon}=\frac{-\tfrac{1}{2}\chi^{(e)}EL}{\varepsilon/\varepsilon_0}=-\frac{(\varepsilon_r-1)EL}{2\varepsilon_r}, \quad (15)$$

where we note that the polarization $P^{(m)}=-\tfrac{1}{2}\varepsilon_0\chi^{(e)}E$ is of magneto-electric origin, is diamagnetic, and equals half the usual electric polarization. In Equation (15) use has also been made of the relationship $\chi^{(e)}=\varepsilon_r-1$ between the electric susceptibility $\chi^{(e)}$ and the relative permittivity $\varepsilon_r=\varepsilon/\varepsilon_0$. Substitution of Equations (14) and (15) into Equation (13) results in a stored energy of $$U=\frac{1}{2}\frac{\varepsilon_0\varepsilon_r A}{L}\left(\frac{(\varepsilon_r-1)EL}{2\varepsilon_r}\right)^2. \quad (16)$$

In the focal region of a fundamental Gaussian beam of radius $\omega_0$, the relevant area and confocal parameter are given by $$A=\pi\omega_0^2 \text{ and} \quad (17)$$

$$L_{conf}=\frac{2\pi\sqrt{\varepsilon_r}\,\omega_0^2}{\lambda}. \quad (18)$$

Hence, if one ignores depletion of the optical pump source, the expression for energy stored in the medium as the result of interacting with a Gaussian beam over the length $L_{conf}$, is $$U_{max}=\frac{\varepsilon_0\pi^2\omega_0^4}{4\lambda\sqrt{\varepsilon_r}}(\varepsilon_r-1)^2 E^2. \quad (19)$$

When the pump source is laser light, the wavelength in Equation (19) is that of the laser and $\varepsilon_r$ is the permittivity at the laser wavelength. When the pump source is a solar input, representative values near the peak of the solar spectrum may be assumed. In the latter case, it is important to note that the power conversion is operative at all wavelengths in the solar spectrum that fall within the transparency range of the conversion material. Hence $\varepsilon_r$ is determined by the off-resonance susceptibility and the entire spectrum is useful for power conversion.

For efficient optical power generation, the energy storage process that develops charge separation must be repeated as rapidly and as often as possible. In the case of sunlight, the direction of propagation of light in the slab should therefore alternate at a high rate $\Omega$. Because a risetime of charge separation faster than 100 fs has been measured, it is virtually instantaneous compared with attainable values of $\Omega^{-1}$. Hence power extraction via conducting electrodes applied to the surface of the slab will be limited chiefly by $\Omega$, assuming that the focused intensity achieves magnetic saturation. Assuming that all the stored energy is extracted during each cycle of beam reversal, the maximum generated power is expressible as $$P_{max}=\frac{\varepsilon_0\pi^2\omega_0^4}{2\lambda\sqrt{\varepsilon_r}}(\varepsilon_r-1)^2\eta_0\Omega I, \quad (20)$$

where $\eta_0$ is the electromagnetic impedance of vacuum and I is the focused optical intensity.

Figure 6:
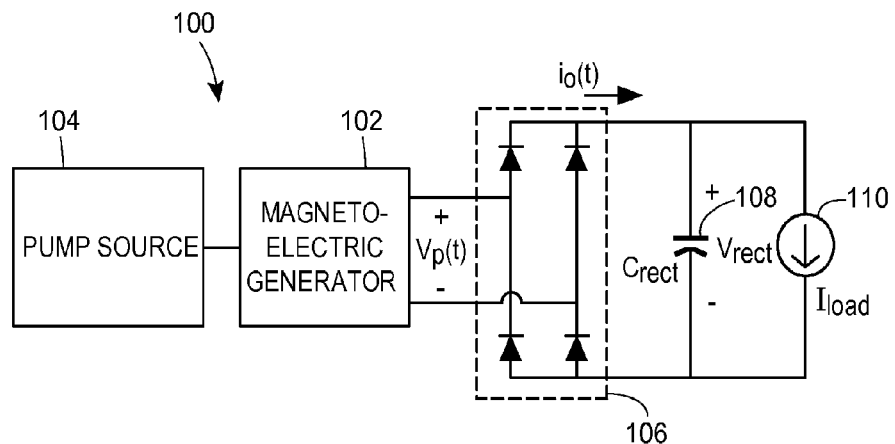
FIG. 6 illustrates a circuit diagram of an embodiment of AC-DC conversion circuit configuration that may be used for energy harvesting from time-varying capacitive energy sources in accordance with some embodiments herein.

The magneto-electric photovoltaic (MPV) process may be implemented in practical power generation applications replacing other known capacitive energy sources, such as piezoelectric elements. An example power conditioning circuit 100 for a repetitively charged capacitive source is illustrated in FIG. 6. Similar to a piezoelectric drive in which mechanical oscillations have been shown to efficiently generate capacitive energy from piezoelectric elements, FIG. 6 illustrates a magneto-electric generator 102 which is fed by a pump source 104, for example, a pulsed laser beam or other coherent light source or a stochastic light source such as solar light, having threshold pumping conditions as set forth herein. The magneto-electric generator 102 may be, for example, a transparent dielectric material, such as crystals, ceramics, dielectrics, insulating polymers, glasses and liquids. The magneto-electric generator 102 converts the light from the pump source 104 into oscillating capacitive charge that is harnessed by a diode rectifier block 106 and fed into a pulse-smoothing capacitor 108 and possibly a DC-to-DC converter in order to drive an electrical current load 110. This oscillating capacitive charge may be made to alternate at a high rate between the forward and backward directions through the energy conversion medium by rapidly and periodically reversing the direction of propagation of the light. The load 110 can then be driven by this DC current source produced solely from conversion of optical pump light energy to electrical impulses, based on the optical charge separation techniques described herein. The embodiment of FIG. 6 is described in further detail below.

Gaussian Laser Beam Conversion

Estimates of the power levels and efficiencies of a converter based on magnetic charge separation can be made using Equation (20). This equation incorporates the relationship between the length $L_{conf}$ of the region over which focusing of a Gaussian beam can be maintained and the corresponding focal spot size $\omega_0$. Hence it will be applied first to estimate optical-to-electric power conversion of a single mode laser beam, under the assumption that the focused intensity is adequate to saturate the chosen magnetic conversion medium. Then, a simple extension involving guided waves will be applied to remove the constraint between sample length L and spot size. This greatly improves efficiency and makes solar power conversion possible.

To estimate the optical-to-electric power conversion possible with a 1 kW fundamental Gaussian beam, we consider focusing it to a spot size of $\omega_0$=50 μm in a sample of sapphire of length $L_{conf}$=4.45 cm. Taking the relative permittivity and wavelength to be $\varepsilon_r$=3.115 and λ=800 nm respectively, an extracted power of $P_{max}$=1.04 W is obtained. That is, the conversion efficiency is found to be just $\eta=P_{extr}/P_{in}$=0.114%.

Note that if the light were focused into an optical fiber of length L, it would be confined over lengths much longer than $L_{conf}$, regardless of spot size. Hence we next consider a sapphire fiber of length L=10 m, removing the constraint between sample length L and $\omega_0$ given by Equation (18). Single-crystal sapphire fibers have a favorably high index, high thermal conductivity, and can be grown in meter lengths by the laser-heated pedestal growth method. The use of the parallel-plate capacitor formula is still justified since fringing fields can be neglected when the light is guided in a fiber. In this situation, the expression for extracted power becomes $$P_{max} = \frac{\varepsilon_0 \pi \omega_0^4 L}{4\varepsilon_r}(\varepsilon_r - 1)^2 \eta_0 \Omega I. \quad (21)$$

For the same input power of 1.0 kW and a fiber core radius of $\omega_0$=50 μm, the extracted power is now 0.299 kW at $\Omega$=25 MHz. Under these conditions, ignoring pump depletion, the theoretical conversion efficiency climbs to η=30%.

Solar Power Conversion

Solar power generation currently emphasizes photovoltaic (PV) energy conversion performed in relatively complex, expensive semiconductor structures (solar cells) where light is absorbed and then converted to free electron-hole charge pairs (excitons) inside opaque media. Ferroelectric materials are also under active investigation as potential photovoltaic sources. Here however, an entirely new approach is proposed, based on magnetic charge separation in unstructured—and therefore much less expensive—insulating materials.

Conventional solar cells require costly fabrication, often with toxic ingredients. The energy conversion process itself, particularly in high-efficiency designs, produces considerable waste heat, which has to be removed. Additionally, the conversion material is opaque. For megawatt-class solar power generators, this means that large areas of the earth's surface are deprived of natural illumination, resulting in undesirable environmental consequences. These disadvantages can be remedied using the magnetic energy conversion techniques described herein. Some advantages of the present approaches are that they do not require semiconductors and produce little waste heat. Furthermore it can achieve high conversion efficiency in safe, transparent dielectrics while transmitting to the ground any light not directly converted into electricity.

The MPV conversion process herein proposed as a renewable energy source is based on parametric resonance in the motion of bound charges within undoped dielectrics. This previously unknown nonlinear optical effect produces static charge separation in atoms irradiated with intense light. A collection of illuminated atoms thereby forms an "optical battery." The work done by the pump light to charge such an optical capacitor is small, but can be used to power an external circuit in the same manner as energy-harvesting from piezoelectric devices. Very rapid repetition of the charge and discharge cycle can result in an efficient, high power electrical energy source.

By tradition, magnetic effects are expected to be extremely weak at optical frequencies. In fact they are usually neglected altogether. This is due to the fact that the multipole expansion limits the magnitude of static magnetic dipole (MD) moments to <$10^{-5}$ times the magnitude of the electric dipole (ED) moment in the same bound-electron system. However, as discussed above optically-induced, dynamic magnetization can readily compare in strength to more familiar electric polarization when the response is nonlinear. The maximum magnetic moment per atom in dielectrics is then observed to be fully one half the electric dipole moment.

Figure 16:
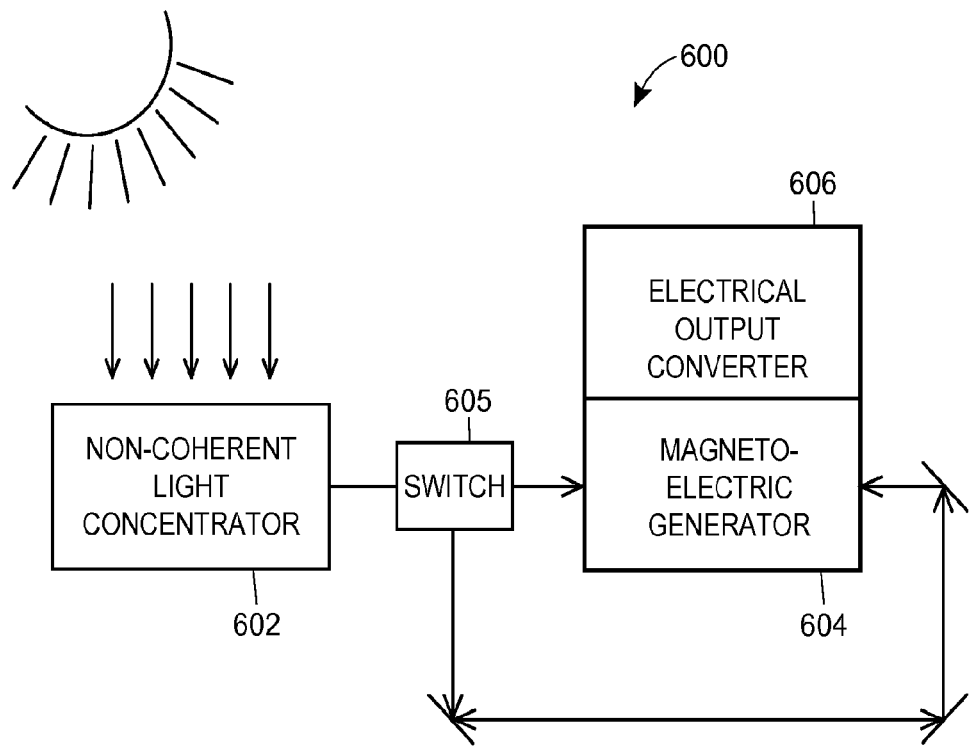
FIG. 16 illustrates an example of an energy conversion circuit as may be used with non-coherent light sources, such as solar energy.

As shown in FIG. 16, a generator 600 includes a concentrator element 602 positioned to collect and concentrate a light output from a non-coherent light source. In the illustrated embodiment the light source is solar energy. However, the light source may be any suitable stochastic light source. In any event, on a sunny day at low latitudes, a spherical solar concentrator of diameter 1.0 m, for example, may collect power roughly equal to that considered above, namely 1 kW. The concentrator 602 may be assumed to be an f1 optic whose focal length equals its diameter. In practice, this will focus the sunlight as tightly as is practical. The sun subtends a relatively large angle $\alpha$=4.67 mrad at earth, so sunbeams are not Gaussian beams. Instead, the focal image size $\omega_0$ is a fixed fraction of the radius R of the concentrator: $\omega_0$=4.67×10$^{-3}$ R. For collected powers in the kW range, the focal spot size is therefore much larger than in the earlier estimates for a Gaussian beam source. The available focal spot intensity is limited to approximately $I_{avail}$~1.46×10$^7$ W/m$^2$, which is considerably lower than the intensity required for example to saturate the optical magnetization in CCl$_4$ where $I_{sat}$ exceeds 10$^7$ W/cm$^2$. The concentrator 602, thus, focuses the received non-coherent light to an intensity sufficient to exceed the threshold intensity of the magneto-electric converter 604 formed of a medium chosen for optical to electrical conversion. In the illustrated example, as a power generator source, the light output from the concentrator 602 is supplied to a switch 605 that functions to reverse the direction of propagation of light within the converter 604. Switching of the direction of the propagation of light is effected by the switch 605 and a reflector ring formed by right angle reflectors. The switch 605, which may perform optical switching at frequency rates, $\Omega$, commensurate with AC power generation. The light from the concentrator 602 is focused into the magneto-electric converter 604 at a focal spot, where depending on the state of the switch 605 that incident light is coupled into the converter 604 through a left side face or a right side face. The converter 604 may be a bulk substrate material in some embodiments, while in other embodiments, the converter 604 is implemented as one or more fiber waveguides confining the incident light output through total internal reflection. The converter 604 may be a fiber as well. While reduction of the magnetic saturation intensity in materials specifically designed for this purpose is anticipated, the availability of intensities lower than $I_{sat}$ will still furnish a magnetic susceptibility of $\chi^{(m)}=-(I_{avail}/I_{sat})^{1/2}(\chi^{(e)}/2)$. Below the magnetic saturation intensity ($I_{avail}/I_{sat}$<1), the extractable power is given by $$P_{out} = \frac{\varepsilon_0 \pi (\varepsilon_r - 1)^2}{4\varepsilon_r} \omega_0^2 L \eta_0 \Omega \left( \frac{I_{avail}^2}{I_{sat}} \right). \quad (22)$$

The earlier discussion of FIGS. 3-5 showed that the charge separation effect of interest is not significantly reduced by dephasing or depolarization at rates approaching the optical frequency itself. Unlike interactions between linear oscillators, the transfer of energy between the electric and magnetic degrees of freedom of light resists disruption and is irreversible. Hence coherent light is not needed to drive the magneto-electric power generation described here. Taking this into account and using the expression for $P_{out}$ in Equation (22), the output of a solar converter based on magneto-electric conversion can therefore be accurately predicted. As an example, we consider implementing a generator with a $\phi$=1 m diameter concentrator (602), a 1-cm diameter bundle of sapphire fibers each of which has a length L=10 m (604), and external circuitry (606) formed of several 50/1 step-down transformers and semiconductor rectifiers with reverse breakdown voltage ratings of $V_B$≥600 V for power conditioning. More broadly, the electric output converter circuit 606 takes the generated electrical current or voltage from the magneto-electric converter 604 and produces an output electrical current or voltage, respectively, that has been converted to a designed current or voltage range, at a desired duty cycle in DC. The external circuit 606 may be coupled to the converter 604, for example, via transparent electrodes placed on the entrance and exit faces by which light enters and leaves the converter, or via coils or electrode structures on the sides of the converter in inductive designs. These electrode structures may be thin film electrodes depending on the size of the converter. They may be sized to increase current or voltage collection and are to be positioned along directions of greatest electron mobility. The electrodes may be formed on the optical converter substrate by printing on the converter, spin coating, mechanical bonding, thermal bonding, and other known electrode forming techniques. According to Equation (15), and assuming $I_{avail}/I_{sat}$=0.1 in a fiber core with the permittivity of sapphire, the end-to-end voltage generated in each fiber of the bundle is V=3.56×10$^5$ Volts. Using a representative wavelength of 0.6 µm for sunlight, and a beam switching rate of $\Omega$=25 MHz as before, the extractable power is 29.7 W, yielding a theoretical efficiency of nearly 3%. Higher conversion efficiency is possible in materials with intensity ratios higher than $I_{avail}/I_{sat}$=0.1.

Capacitive and Inductive Systems

The scheme for optical power conversion described above is basically capacitive in nature. Hence the voltages that develop across the conversion medium approach the megavolt range when the efficiency is pushed to high values, for example by extending fiber length. Although power extraction at these high voltages can be handled using transformers and robust electronics, the identification of materials with lowered intensity requirements will reduce the voltage levels to more manageable levels. Also, non-capacitive schemes offer alternatives. By using pulsed or chopped input light, inductive implementations of this power generation scheme can be imagined that would exploit the transient, optical magnetization of the medium to produce current flow inductively. By passing the light through an array of conducting split rings whose diameters lie parallel to the propagation axis, single cycle voltage waves would be generated by each pulse passing through the medium, according to Lenz's Law.

Summary of Power Conversion and THz Generation Mechanism

In previous sections above, we have described how a new quadratic optical interaction can mediate quasi-static charge separation and THz emission in transparent dielectric materials; and we have proposed a magnetic photovoltaic power generation scheme that relies on displacement currents in insulators, avoiding the absorption and electron-hole pair production that typify semiconducting solar cells. Dephasing and depolarization of the pump light result in negligible reductions in the expected charge separation and magnetic energy storage. Hence for sufficiently high input power from a laser or solar concentrator, particularly in conjunction with the use of a waveguide and optimized conversion media, optical-to-electrical power conversion efficiencies of ~10% or more should be readily attainable from a variety of light sources using fast beam switching.

Conditions for Efficient Conversion

Figure 7:
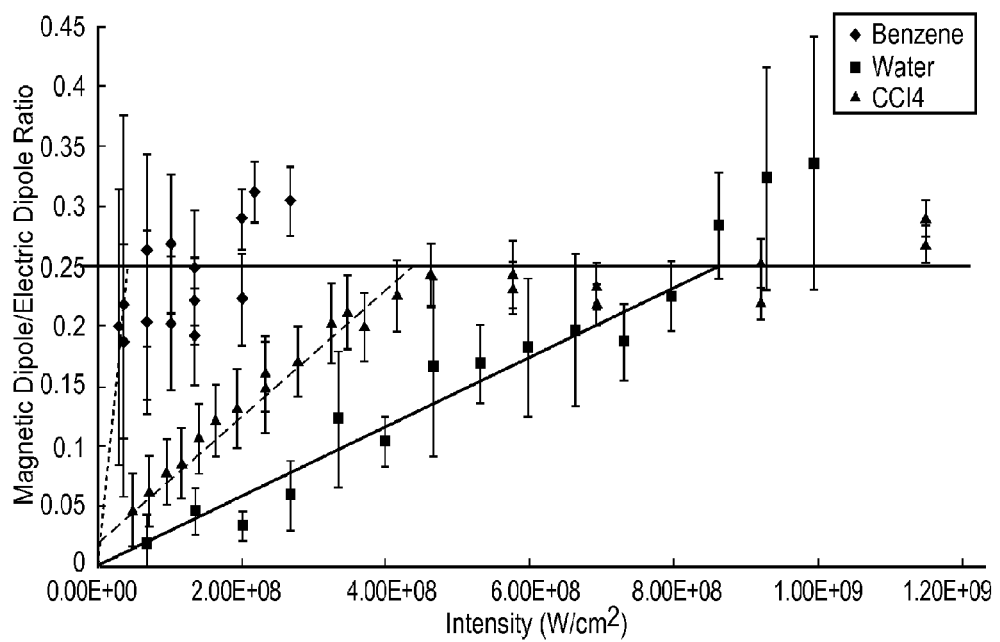
FIG. 7 illustrates a plot of ratios of magnetic and electric dipole scattering intensities in water (squares), $CCl_4$ (triangles), and benzene (diamonds). The slopes of the experimental curves are clearly different in different media.

Identification of the threshold for magnetic response from photon pumping is important, as the intensity needed to elicit maximum magnetic response (or to achieve "magnetic saturation") can vary greatly from one material to another. The conversion techniques described above can be used in various materials including, crystals, ceramics, dielectrics, insulating polymers, glasses and liquids. Evidence for this is shown in FIG. 7, where the rising slopes of magnetic scattering intensities are seen to differ by an order of magnitude in three representative, transparent liquids. Benzene is the most responsive, $CCl_4$ is next, and water requires the highest input intensity to maximize the magnetic dipole to electric dipole scattering ratio (although the maximum MD/ED intensity ratio is the same for all samples, namely 0.25). The implication is that the aromatic ring of the benzene structure may be beneficial in promoting magnetic response. The conclusion may be drawn that chemical structure affects magnetic response, even though the exact nature of features that enhance magnetic response remain to be determined. The radial slope of the intra-molecular potential that governs the response of electrons to applied electric fields has been accurately determined for many compounds. However, we know of no measurements reported in the scientific literature on azimuthal restoring forces within molecules subjected to the torsion of a high-frequency magnetic field. Hence an empirical approach (described below) will be adopted to identify "good" versus "bad" material characteristics for optical magnetism.

Example Materials for Efficient Conversion

This section describes examples of media prepared for evaluation and used as energy conversion materials. For solar power generation applications, what is needed is non-conducting (dielectric) medium that contains no reflective interfaces, does not absorb incident light and liberates no free charges.

Many molecular compounds have delocalized orbital structures that are expected to facilitate optical magnetism, a conclusion that may be drawn directly from FIG. 7. In the data of this figure, it may readily be noted that the most conjugated (and therefore delocalized) material, namely benzene, develops the maximum MD/ED ratio at the lowest intensity. However, not many form solids that conduct heat well at room temperature or are robust enough to serve as power conversion media. Silsesquioxanes (SQs), especially phenyl-silsesquioxanes, are exceptional in this regard and exemplify a group of materials whose variable electron density and adjustable delocalization properties are of central interest. Another class of materials that is suited to thermal management for energy conversion is transparent ceramics. Hence powders that have been processed transparent also provide dielectric solids suitable for the current application.

Figure 9A:
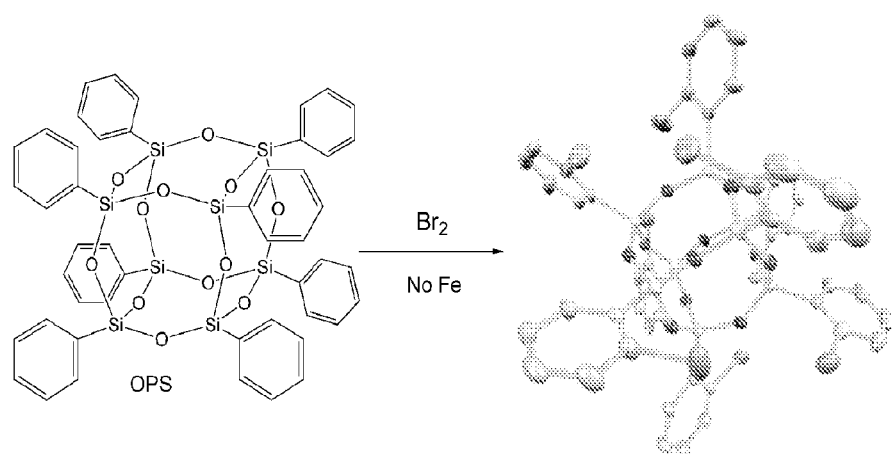
FIG. 9A illustrates [o-BrPhenylSiO$_{1.5}$]$_8$ synthesis, single crystal structure.
Figure 9B:
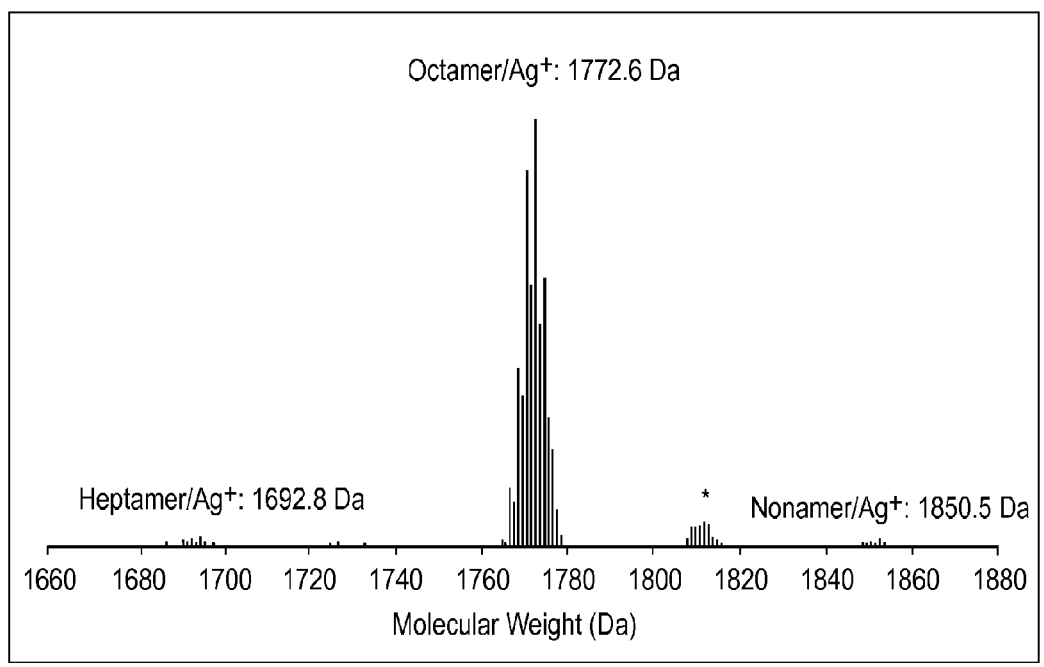
FIG. 9B is a plot of the matrix-assisted laser desorption/ionization (MALDI) time of flight mass spectrum of the single crystal structure.
Figure 10A:
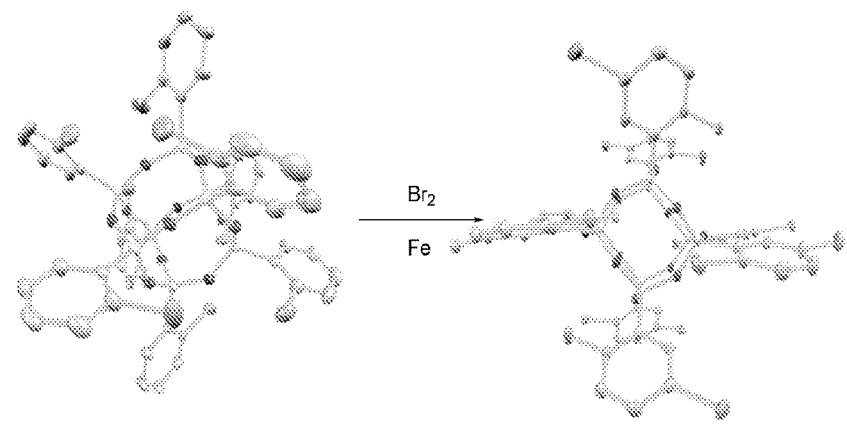
FIG. 10A illustrates [2,5-Br$_2$PhenylSiO$_{1.5}$]$_8$ synthesis, single crystal structure.
Figure 10B:
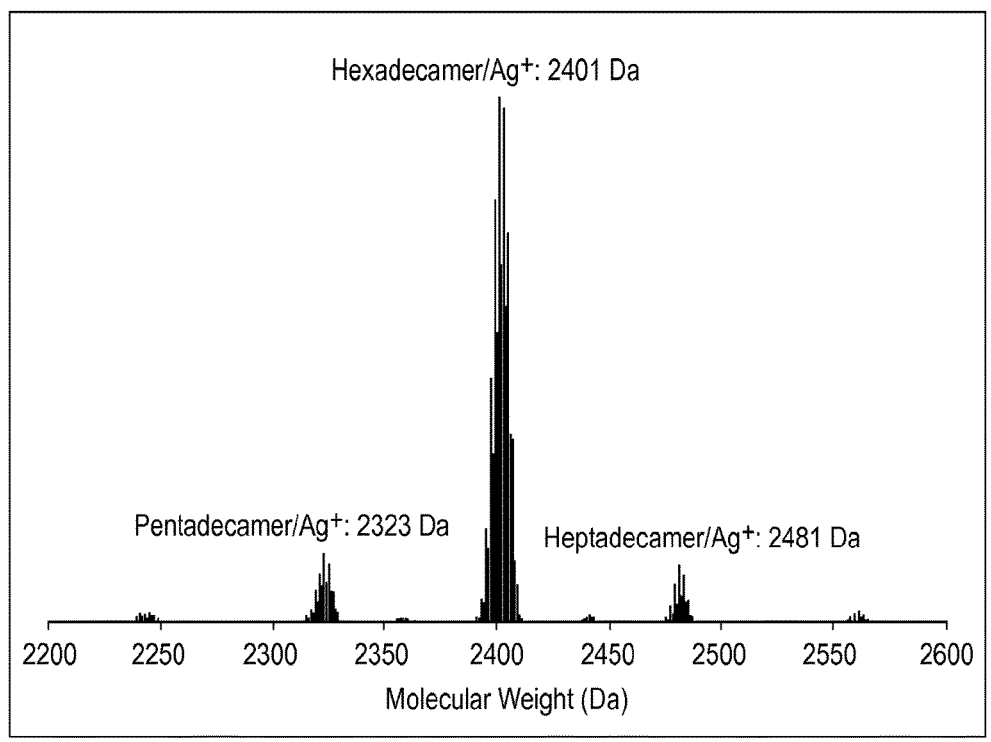
FIG. 10B is a plot of the MALDI TOF-mass spectrum of the single crystal structure.
Figure 11A:
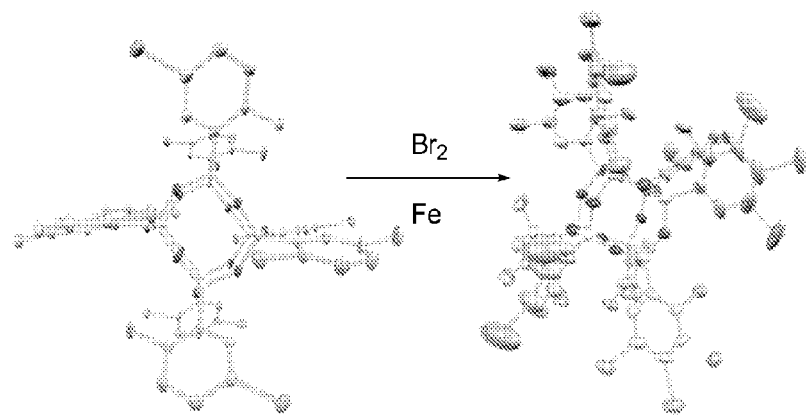
FIG. 11A illustrates [Br$_3$PhenylSiO$_{1.5}$]$_8$ synthesis, single crystal structure.
Figure 11B:
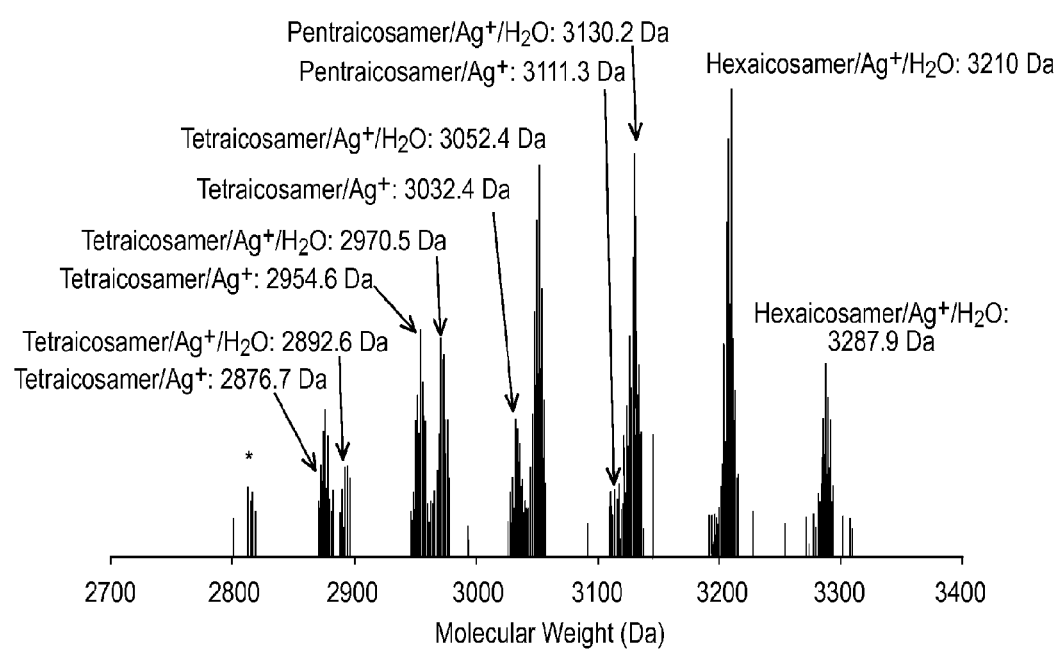
FIG. 11b is a plot of the MALDI TOF-mass spectrum of a plurality of structures.

One of the significant advantages of choosing SQ systems is that they can provide very high densities of functional groups in very small volumes. The synthesis of SQ materials makes it possible to adjust the degree of conjugation and/or electron density per unit volume in the appropriate fashion. Hence they furnish a suitable avenue for optimizing the structure of magneto-electric conversion materials. Soluble materials of this type can be synthesized with very low to very high densities of bromines in essentially the same volume as shown in FIGS. 9-11. In addition to these three T8 SQs the T10 and T12 analogs can be synthesized; and all the halogens on the T8, T10 and T12 cages can be replaced by phenyl groups, diphenyl groups, napthalenes, anthracenes, etc. It is important to note that the bromine-substituted compounds may have the highest densities of bromine of any molecule ever made. Also, all of these compounds have excellent thermal stabilities. Consequently materials like these embody the characteristics thought to be favorable to produce optically-induced magnetic effects in the context of energy conversion, namely high adjustable election density, adjustable degrees of delocalization, and high thermal conductivity in a transparent solid. Whether a material is "better" or "worse" than another for magneto-electric conversion can be determined experimentally as described next.

Methods for Optimizing Conversion Media

Figure 8A:
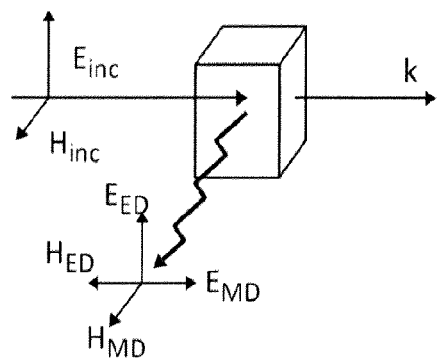
FIG. 8A is a schematic illustration of scattered light geometries for the observation of vertically-polarized electric dipole.
Figure 8B:
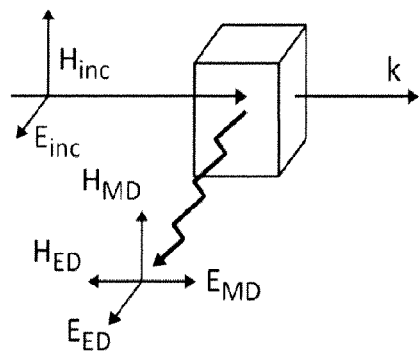
FIG. 8B is a schematic illustration of scattered light geometries for the observation of horizontally-polarized magnetic dipole radiation.

The data of FIG. 7 provide a concrete example of how quantitative comparisons of the relative intensities of magnetic and electrical dipole light scattering may be used to compare the magnetic susceptibility candidate. These comparative measurements of induced magnetization constitute a method that permits electric dipole (ED) radiation to be distinguished from magnetic dipole (MD). In the example of FIG. 7, the more desired materials will be those determined to have the steepest slope in scattering measurements. The higher the slope, the lower the threshold intensity requirement for conversion, which is why benzene and data on the far left of FIG. 7 are the preferred among the three materials shown. In any event, this characterization technique can be used to evaluate and optimize materials for optically induced magnetic technology by measuring the MD/ED intensity ratio in a 90 degree geometry, as depicted in FIGS. 8A and 8B, and selecting the material which has the largest ratio at the smallest intensity.

Two methods can be used for direct comparisons of the induced magnetic response of all samples, namely elastic light scattering and THz pulse detection.

The first method uses light scattering experiments of exactly the type used to record the data in FIG. 7. For this purpose an amplified Er laser source (Clark-MXR CPA 2001) that is directed into the interaction region may be used. There, scattered light is collected at ninety degrees, polarization-analyzed, and detected with a photon-counting apparatus. By comparing the measured slopes of induced magnetic response in various samples, it is possible to identify those that respond at the lowest intensities. In addition, a solar simulator, consisting of a 300 W xenon discharge source with an effective area <1 $cm^2$, can be substituted for the laser source, to make measurements with white light in the intensity range ~$10^8$ W/$m^2$ in the best samples. In these experiments, since the source will be continuous, the induced voltage across the sample will be detected directly as depicted in the lower left portion of FIG. 12. The electrical signal can be converted to AC by spinning the sample. This enables synchronous detection of the output.

Figure 12:
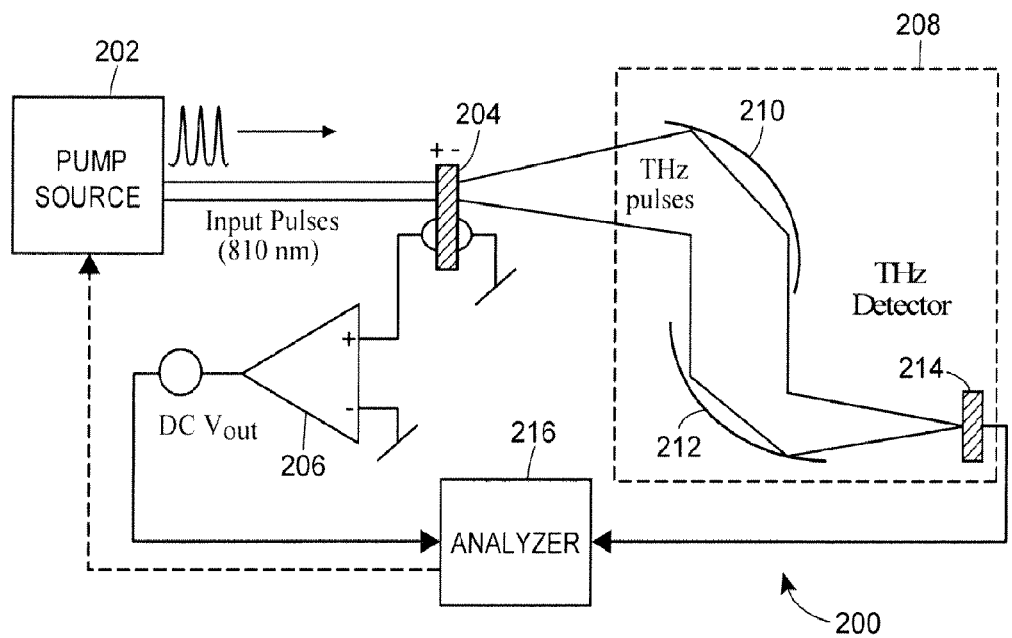
FIG. 12 illustrates a schematic of an apparatus for measuring the time-averaged longitudinal DC voltage induced by moderately intense light pulses across a transparent sample, and the associated THz radiation emitted in a forward-directed cone.

FIG. 12 illustrates a system 200 for analyzing materials to determine conditions for magneto-electric conversion in accordance with embodiments herein. An input beam is produced by a pump source 202, which in the illustrated embodiment produces pulsed beams centered at 810 nm. The input beam is incident on a sample 204 formed of a holder and sample material under examination. In the illustrated embodiment, the sample 204 is connected across a voltage ground and signal amplifier 206, which receives an output voltage from the sample 204, induced by the input beam, and amplifies that voltage to produce a DC output voltage.

To measure THz pulse conversion and generation from the sample 204, a collector stage 208 formed of two off-axis THz reflectors 210 and 212 is provided for collimating and then focusing the divergent THz output beam from the sample 204. A THz detector 214 is then placed at the focal point of the second reflector 212 for terahertz detection. In the illustrated embodiment, both the detector 214 and DC output from the amplifier 206 are provided to a data analyzer 216, which may include a computer or other processor device (e.g., a network analyzer) that analyzes the received data to determine whether the material within the sample 204 is suitable for magneto-electric conversion. In some embodiments, the analyzer 216 is coupled to or a part of system controller that also controls operation of the pump source 202, to adjust the pumping conditions of the source 202 for more optimal determination of the conditions under which the sample material is suitable for magneto-electric conversion.

For the second detection stage, i.e., the THz detection, direct comparisons of optically-induced charge separation may be performed in all samples using the THz detector 214. For example, a steady train of mode-locked pulses from an (unamplified) Ti:Sapphire oscillator, acting as the pump source 202, may be focused inside the sample 204 to generate an impulsive separation of charge in the absence of any applied bias. This surface charge, or the voltage accompanying it, constitute the signal in these measurements. During each optical pulse a dipole moment forms that is similar to that shown in FIGS. 1B, 2A and 2B, but it will be of such short duration (~100 fs) that its spectrum will extend into the THz range as dictated by Fourier transform relations. The resulting THz output pulses are collected into the stage 208, from which comparative measurements of THz intensity permit an evaluation of the suitability of different compounds for optically-induced magnetic response.

Optical Charge Separation to Electrical Energy Conversion

The light-induced charge separation stores energy in the form of a surface charge on intensely illuminated dielectrics. The time required to charge the material is very short (<100 fs response time in our experiments), and the total charge is also very small. Hence to convert optical energy efficiently to electric current from such an "optical battery," the induced electrode charge must be drawn off quickly and the direction of propagation of light reversed so that the process can be repeated as many times per second as possible. To switch the propagation direction, electro-optic beam switching at a frequency $\Omega$ may be used. In this way a high-frequency source of current ($I_s=Q\Omega$) can be produced that will be coupled with 95% efficiency to Li-battery storage via DC-to-DC conversion using existing types of circuitry. The extracted power is $P=\Omega Q^2/2C$ where C is the capacitance of the structure. If the conversion medium is an optical fiber, the internal field will be uniform and the usual formula for a parallel plate capacitor is valid. For a 1 kW laser focused to a spot diameter of only 100 μm in a 10 m silica fiber, and $\Omega=25$ MHz, the output power is predicted to be P=258 W (efficiency $\eta=25.8\%$).

Solar radiation cannot be focused nearly as well as laser light. Consequently, the intensities available to drive the optical conversion process described above are lower for sunlight than in the case of diffraction-limited laser beams. A 1 m diameter concentrator with a 1 m focal length can only achieve $I_{avail} \sim 1.46 \times 10^7$ W/m$^2$ in full sun at southerly latitudes. Additionally, sunlight is incoherent. So its effectiveness as a driving force in a coherent nonlinear optical process might seem doubtful. However, it is shown herein, through preliminary simulations of the stochastic fluctuations typical of light from the sun, that optically-induced charge separation diminishes less than 5% for light as incoherent as sunlight. This remarkable persistence of the MPV effect for incoherent light is due to its magnetic origin. The important role played by the optical magnetic field in producing charge separation ensures that the effect is "unipolar" in time and space—it rapidly accumulates even for poor driving fields.

With a suitable material illuminated under the threshold conditions required for energy conversion through photon pumping, a substrate is provided in the circuit 100 of FIG. 6 using the photon pumped substrate of the magneto-electric generator 102 to produce AC current across the load, $i_p(t)$. The substrate forming the generator 102 therefore may be a non-conducting material such as a glass, polymer, crystal, liquid, transparent ceramic, silsesqualoxane derivative, or the like. In some embodiments, the pump source 104 pumps, into this substrate, a pulsed laser output having a characteristic pulse width of less than 100 fs and an energy level above the threshold for inducing saturated magnetic dipole response in the substrate to produce an alternating electrical current across the substrate. This pumping converts the substrate into a magneto-electric photovoltaic source (MPV substrate). In some embodiments, an AC-DC rectifier (106) is added to convert the produced AC current into a DC current or voltage.

The circuit of FIG. 6 may be used to determine the point of optimal power flow (optimal current flow) for the MPV by adjusting the pump laser beam in response to measured DC current or voltage at a load.

To determine power flow characteristics, the pumped MPV substrate may be modeled as a sinusoidal current source $i_p(t)$ in parallel with its internal electrode capacitance $C_p$. The magnitude of the current $I_p$ varies with induced magnetization of the substrate. The MPV generates an AC voltage while electrochemical batteries require a DC voltage, hence the first stage needed in an energy harvesting circuit is an AC-DC rectifier (106) connected to the output of the substrate, as shown in FIG. 6. The DC filter capacitor $C_{rect}$ is assumed to be large enough so that the output voltage $V_{rect}$ is essentially constant, although this need not be the case. The load is modeled as a constant current source $I_{load}$; and the diodes are assumed to exhibit ideal behavior.

Figure 13:
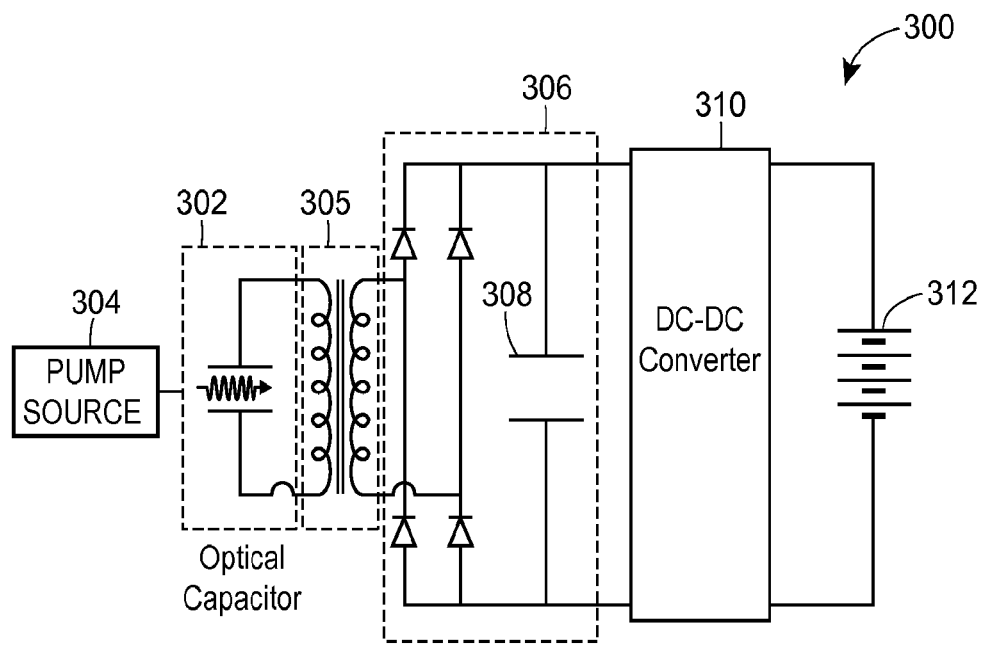
FIG. 13 illustrates a circuit diagram of an embodiment energy conversion circuit in accordance with embodiments herein and similar to that of FIG. 6 but having a DC-DC converter.

The magnitude of the polarization current $I_p$ generated by a MPV substrate used to formed a magneto-electric generator, and hence the optimal rectifier voltage, may not be constant. This creates the need for flexibility in the conversion circuit, i.e., the ability to adjust the output voltage of the rectifier to achieve maximum power transfer. To facilitate the attainment of the optimal voltage at the output of the rectifier, a DC-DC converter may be placed between the rectifier output and the battery as shown in FIG. 13. In FIG. 13, a converter 300 includes an MPV substrate forming an magneto-electric generator 302 pumped by an output from a pump source 304, similar to that described above for FIG. 6, where the generator 302 produces an oscillating current and high voltage output. It is noted that the generator, like that of FIG. 6 and elsewhere described herein, operates as an optical capacitor, storing optical energy in the form of electrical oscillating voltage. In any event, in the illustrated example an optional transformer stage 305 is used to convert the voltage from the generator 302 stepping the voltage down to levels appropriate for the example battery application illustrated. The stepped down AC voltage from the generator 302 is fed to an AC-DC converter stage 306 formed of a set of rectifying diodes feeding a pulse-smoothing capacitor 308, similar to that of FIG. 6. An optional DC-DC converter 310 is coupled between the output of the AC-DC converter 306 and a battery source 312, for example to perform impedance or voltage matching to the DC signal prior to battery storage. Typically the controller of a DC-DC converter is designed to regulate the output voltage; however, in the circuit 300 the converter 310 is operated to maximize power flow into the battery 312, which may be a Li-ion battery, for example. If effective, the MVP substrate would be at peak power, which may correspond to the output voltage of the rectifier $V_{rect}$ being maintained at its optimal value, approximately one-half the open-circuit voltage, as described previously. While the example of FIG. 6 is described as producing an output current, in other examples the output may be a voltage output, at the load stage.

The circuit 300 is able to maximize the power flowing into the battery 312. As the battery voltage is essentially constant or changes very slowly, this is equivalent to maximizing the current into the battery, $I_{battery}$. By sensing this current, the duty cycle can be adjusted to maximize it. A control scheme such as this is general enough to be effective for many dc-dc converter topologies.

Terahertz Radiation Generator

Figure 14:
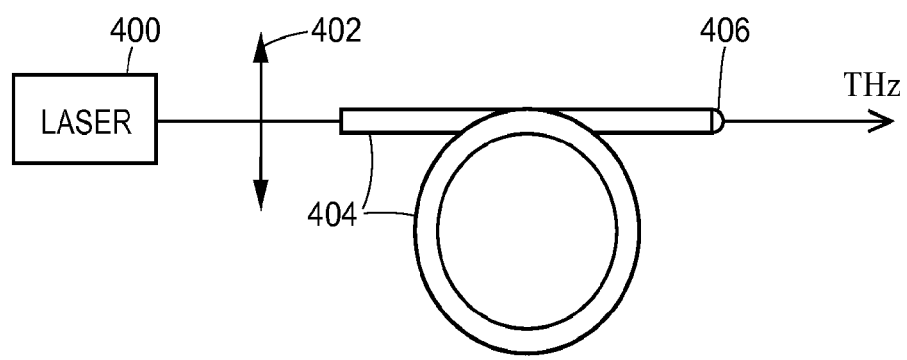
FIG. 14 illustrates a schematic of a Terahertz radiation generator having a laser source emitting ultrashort pulses, beam coupling optics to insert the laser output into the generator medium (which may be an optical fiber) and collimating optics for the THz output wave.

FIG. 14 illustrates a system that has charge separation mechanism adapted for the generation of Terahertz radiation, under conditions that are different from those for optical power conversion. For THz generation, a laser source 400 produces ultrashort pulses with a pulse duration of less than $\tau_p=10^{-12}$ s and a peak intensity exceeding the aforementioned threshold for saturation of the induced magnetization of the generator medium are required. A beam coupler 402 focuses the ultrashort pulses into fiber 404, which confines the light to a small diameter and acts as the THz conversion medium.

Pulses with desired properties are available from mode-locked laser sources and result in impulsive charge displacement in the fiber 404, by the same mechanism described in the earlier sections of this application on charge separation. Short, intense interactions produce a quasi-static electric polarization polarized parallel to the propagation axis of the pump light, with a spectrum extending into the THz region as dictated by the Fourier analysis of the short pulse duration. The pulses must be passed through a THz generation medium. FIG. 14 illustrates an embodiment where this medium is the optical fiber 404, which confines both the pump light and the THz waves by total internal reflection. At the output end of the fiber 404, the THz radiation is then coupled out of the device by a conical lens 406 or decoupling means.

Magnetic Field Generator

According to Equations (10) and (11), together with the constitutive relation $B=\mu_o H+M$, the specific pumping conditions illustrated in FIG. 7 produce a saturated magnetization M in addition to a static electrical charge whose magnitude is $$|M| = \frac{c}{2}|P|. \tag{23}$$

The production of this magnetization is confirmed experimentally by the experiment of references. A large induced change $\Delta B$ in the internal magnetic field of the sample is also necessarily produced, since $$\Delta B = B - \mu_o H = \mu_o M. \tag{24}$$

The additional magnetic field strength $\Delta B$ can be calculated by combining Equation (23) and (24) for any given value of the optical intensity. For example, if the intensity is $I=10^{12}$ W/cm$^2$ the corresponding electric field amplitude in free space is $$E = \sqrt{2\eta_o I} = 2.75 \times 10^9 \left(\frac{V}{m}\right) \text{ and} \tag{25}$$

$$\Delta B = \frac{1}{2}\mu_o \varepsilon_o \chi^{(e)} E.$$

Taking the ordinary (linear) electric susceptibility for transparent optical material to be of order unity ($\chi^{(e)} \sim 1$), because most dielectrics have a refractive index $n=\sqrt{1+\chi^{(e)}}$, which lies between 1 and 2; we find the induced magnetic field change to be $$\Delta B \cong 4.6 \text{ Tesla} \tag{26}$$

This field strength is comparable to the magnetic fields generated by superconducting magnetic coil structures, but the field is not constant in this case. Here, it oscillates at the frequency of the light.

Although the field change in Equation (26) is oscillatory, meaning that its average value is zero, this constitutes a magnetic field generation concept on which new classes of magnetic devices can be based, because the optically-induced magnetic field exerts a large torque on any magnetic moment located in the field. It can also be used to cause magnetic alignment of spins or other magnets in the direction of the axis of the field. It can preserve the orientation of polarized moments in a desired direction or along a desired axis, and could thereby greatly improve spintronic circuits. It also constitutes a magnetic dipole source of electromagnetic radiation of a new kind, since it radiates and does so at high frequency.

Magnetic Field Applications

To generate magnetic fields of the magnitude of that given by Equation (26), intensities of the pump light need to be somewhat higher than those for energy conversion. The reason for this is two-fold. First, as indicated by Equation (25) the magnetic field strength is proportional to the electric field amplitude of the light. $\Delta B$ grows as the square root of the optical intensity, and the calculation of Equation (26) shows that to reach levels in excess of 1 Tesla an optical intensity of $I>10^{12}$ W/cm$^2$ is needed. The materials needed for magnetic field generation are the same as identified for the earlier two applications. Molecular solids with a high density of bound electrons and a high degree of delocalization should provide the largest magnetic response. In addition, a high damage threshold is desirable since higher intensities need to be applied to the sample medium.

Figure 15:
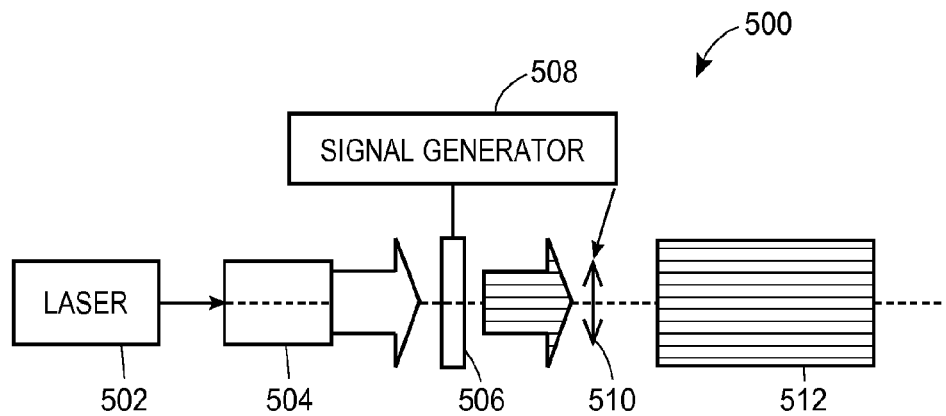
FIG. 15 illustrates a schematic of a magnetic field generator based on light-induced magnetization of transparent insulators. The intensity and frequency distribution versus time of laser output is controlled by a light modulator. Since the magnetic field induced in the medium depends on the square of the intensity at any instant, the programmed intensity distribution versus time and frequency inside the medium determines the induced magnetization in time and space.

This method of generating large magnetic fields has many advantages over existing generators. First, the magnetic field may be produced without bulky electrical coil structure to carry current, as in electromagnets. Second, the magnetic field can be tuned in intensity by merely adjusting the intensity of the pump beam. Third, the magnetic field is generated nonlinearly only at locations where the light field is strongest. Consequently, near a focal point of the pump beam (as an example of a point of high intensity), this provides a unique method of generating a point-like magnetic field region. The size of the region will correspond roughly to the size of the focal spot in this case. Fourth, other unique geometries are possible, such as curved or straight lines of magnetic field, magnetic sheets, beaded lines of magnetic field produced with counter-propagating pump beams, and so on. In principle, with a suitable intensity modulator, any desired 3-dimensional spatial distribution of magnetic field can be programmed into a transparent insulating medium, as indicated in magnetic field inducing system 500 of FIG. 15.

In the system 500, a laser source 502 produces a pump beam that is coupled to a beam expander 504 capable of producing an increased beam width collimated output beam incident upon a light modulator 506. The modulator 506 may be an acousto-optics or electro-optic modulator that is controlled by a signal generator 508 and may modulate received collimated output beam with an information carrying signal. A resulting modulated output beam is provided to an optical imaging stage 510 that focuses the modulating output beam onto a dielectric or semiconducting recording substrate 512. The image stage 510 may be a mechanically and/or electrically controlled stage capable of scanning the modulated output beam laterally (xy plane) across the substrate 512 and longitudinally (along the z axis) into the substrate 512. In this way, an inhomogeneous magnetic field can be selectively induced at different points within the substrate 512. With the substrate 512 formed of a magnetic storage material, such induced magnetic fields are recorded in the substrate 512, for example, for storage of the information from signal generator 508 on the modulated beam Optically-induced magnetic fields can be generated in semiconductors by tuning the pump wavelength into the region of the energy gap. By choosing any wavelength longer than the absorption edge wavelength, a magnetic field can be generated in the bound electron population of the host material, without interfering with conduction band currents. In this way, a large magnetic field can be induced in a medium or circuit for the purpose of preserving spin orientation far longer than the usual dephasing time. This may be very useful in spintronic circuits or quantum bit registers in quantum computers or other devices where the preservation of spin orientation for prolonged times is desirable.

Also, in existing optical read/write magnetic memories, the light has been shown to encode or erase information stored in static magnetic domain structures via the inverse Faraday effect. The inverse Faraday effect produces a very small longitudinal field which has been invoked by others to explain ultrafast precession observations and magnetic domain re-orientation dynamics. With the present techniques, spin preservation or spin-flipping can be induced without the intervention of spin-orbit coupling within individual magnetic atoms. Instead the field generation technique described here produces magnetic fields via charges of the host insulator atoms that can then act directly on the spins of a dilute magnetic dopant species.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein Upon reading this disclosure, those of skill in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A reconfigurable magnetic field generator comprising:
    an unbiased, non-conducting transparent substrate;
    a laser source coupled to pump laser output into the substrate, the laser output having an intensity above a threshold for inducing saturated dipole magnetization in the substrate;
    an optical modulator to control the pump laser output distribution in space, time, and frequency to effect a desired variation of an induced B field amplitude in the substrate; and
    a programmable controller to control the modulator to control the distribution of the laser output and to produce a desired modulation of laser output cross-sectional and temporal intensity.

2. The magnetic field generator of claim 1, wherein the substrate is a semiconductor and the laser output has a carrier wavelength selected to lie within the forbidden energy gap of the semiconductor.

3. The magnetic field generator of claim 1, wherein the substrate is a dielectric material.

4. The magnetic field generator of claim 3, wherein the dielectric material is transparent at optical wavelengths.

5. The magnetic field generator of claim 3, wherein the dielectric material is non-transparent at optical wavelengths.

6. The magnetic field generator of claim 1, wherein the substrate is a magnetic material that contains a static magnetization prior to pumping the laser output into the substrate.

7. The magnetic field generator of claim 1, wherein the substrate is a magnetic material that does not contain a static magnetization prior to pumping the laser output into the substrate.

8. The magnetic field generator of claim 1, wherein the programmable controller is configured to impart information on the laser output through control of the modulator, and wherein the information is stored as magnetic domain structures in the substrate.

9. The magnetic field generator of claim 8, wherein a size and/or geometry of the magnetic domain structures in the substrate varies with the imparted information.

10. The magnetic field generator of claim 1, wherein the programmable controller is configured to impart information on the laser output through control of the modulator, and wherein a size and/or geometry of a spatial distribution of the magnetic field in the substrate varies with the imparted information.

* * * * *